United States Patent
Chun et al.

(10) Patent No.: US 9,328,377 B2
(45) Date of Patent: May 3, 2016

(54) DETECTION OF TARGET NUCLEIC ACID USING A TARGET HYBRIDIZATION AND DETECTION PRIMER

(75) Inventors: Jong Yoon Chun, Seoul (KR); In Taek Hwang, Seoul (KR); Young Jo Lee, Seoul (KR)

(73) Assignee: SEEGENE, INC., Seoul (KR)

( * ) Notice: Subject to any disclaimer, the term of this patent is extended or adjusted under 35 U.S.C. 154(b) by 854 days.

(21) Appl. No.: 13/508,086

(22) PCT Filed: Nov. 28, 2009

(86) PCT No.: PCT/KR2009/007064
§ 371 (c)(1),
(2), (4) Date: May 4, 2012

(87) PCT Pub. No.: WO2011/055875
PCT Pub. Date: May 12, 2011

(65) Prior Publication Data
US 2012/0219955 A1    Aug. 30, 2012

(30) Foreign Application Priority Data

Nov. 7, 2009 (KR) .................. 10-2009-0107262

(51) Int. Cl.
*C12P 19/34* (2006.01)
*C12Q 1/68* (2006.01)

(52) U.S. Cl.
CPC ............ *C12Q 1/6823* (2013.01); *C12Q 1/6818* (2013.01); *C12Q 1/6851* (2013.01); *C12Q 1/6853* (2013.01)

(58) Field of Classification Search
USPC ............ 435/6.12, 91.1, 91.2; 536/24.33
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 5,210,015 A | 5/1993 | Gelfand et al. |
| 6,117,635 A | 9/2000 | Nazarenko et al. |
| 6,248,526 B1 | 6/2001 | Weimer |

(Continued)

FOREIGN PATENT DOCUMENTS

| | | |
|---|---|---|
| EP | 1634962 A1 | 3/2006 |
| WO | 88/10315 | 12/1988 |

(Continued)

OTHER PUBLICATIONS

Kwoh, D. et al., Proc. Natl. Acad. Sci. U.S.A., 86:1173 (1989).

(Continued)

*Primary Examiner* — Kenneth Horlick
(74) *Attorney, Agent, or Firm* — Gianna Julian-Arnold; Saul Ewing LLP

(57) ABSTRACT

The present invention relates to the detection of a target nucleic acid sequence using a target hybridization and detection primer (THD primer). The present invention allows for both a target amplification and a signal amplification by introducing a label into a primer used in PCR reactions, ensuring a real-time target detection by PCR reaction by no use of complicated oligonucleotides. The present invention could completely be free from the troublesome matters and shortcomings associated with conventional real-time PCR methods. The present invention allows for successful real-time target detection by using only a labeled primer. This feature makes it possible that the present invention exhibits excellent real-time target detection in multiplex manner.

21 Claims, 27 Drawing Sheets

(56) References Cited

U.S. PATENT DOCUMENTS

| | | | |
|---|---|---|---|
| 6,322,980 B1 * | 11/2001 | Singh | 435/6.12 |
| 6,326,145 B1 | 12/2001 | Whitcombe et al. | |
| 7,344,830 B2 * | 3/2008 | Philpott et al. | 435/5 |
| 2004/0076994 A1 | 4/2004 | Yaku et al. | |
| 2007/0054296 A1 | 3/2007 | Piepenburg et al. | |
| 2007/0099211 A1 | 5/2007 | Aivazachvili et al. | |
| 2009/0081676 A1 | 3/2009 | Chou et al. | |

FOREIGN PATENT DOCUMENTS

| | | | |
|---|---|---|---|
| WO | 89/06700 | | 7/1989 |
| WO | 2006/095981 | * | 9/2006 |

OTHER PUBLICATIONS

Saiki et al., (1985) Science 230, 1350-1354.

Nazarenko et al, 2516-2521 Nucleic Acids Research, 1997, v.25 No. 12.

Whitcombe et al, 804-807, Nature Biotechnology v.17 Aug. 1999.

Indian J Med Res 124: 385-398 (2006).

Tyagi et al, Nature Biotechnology v.14 Mar. 1996.

Bernad et al, 147-148 Clin Chem 2000; 46.

Noonan, K. F. et al., Nucleic Acids Res. 16:10366 (1988).

International Search Report, dated Jan. 10, 2011, issued in priority International Application No. PCT/KR2009/007064.

* cited by examiner

Fig. 1A

5'-cleavage and 3'-extension of the THD primer

A. Hybridization

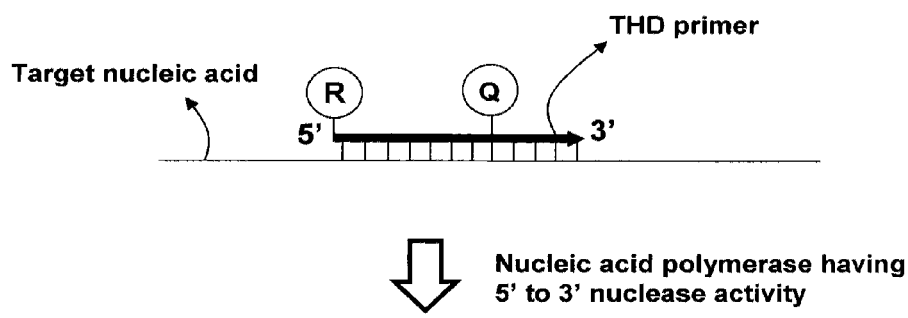

Nucleic acid polymerase having 5' to 3' nuclease activity

B. Signal generation by 5'-cleavage & 3'-extension of the THD primer

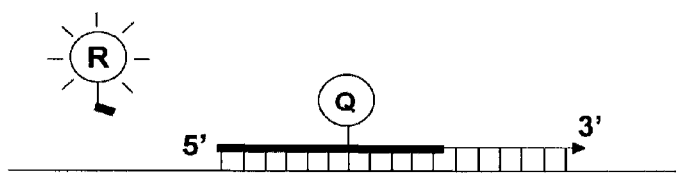

5'-cleavage of the THD primer by the 5' to 3' nuclease activity of the nucleic acid polymerase and 3'-extension of the THD primer by the polymerase activity of the nucleic acid polymerase. A signal indicative of the presence of the target nucleic acid is obtained.

Detection of signal by predetermined time interval

Real-time signal detection

Fig. 1B

5'-cleavage and 3'-extension of the THD primer

A. Hybridization

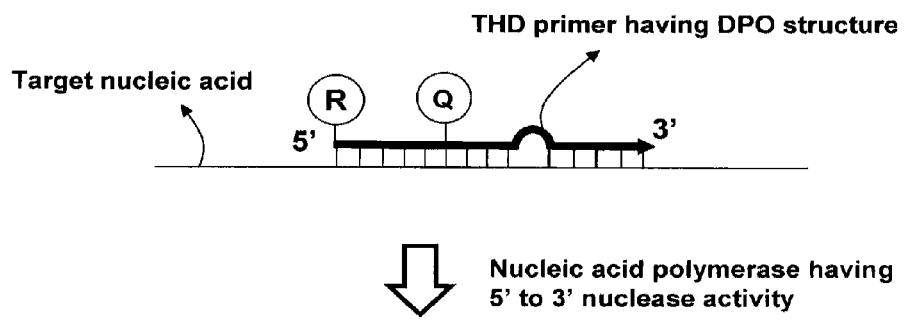

Nucleic acid polymerase having 5' to 3' nuclease activity

B. Signal generation by 5'-cleavage & 3'-extension of the THD primer

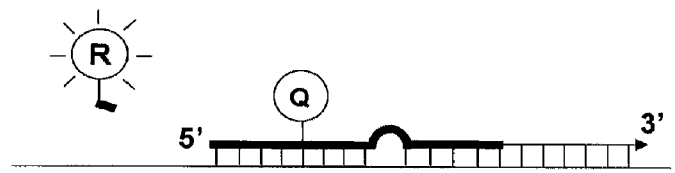

5'-cleavage of the THD primer by the 5' to 3' nuclease activity of the nucleic acid polymerase and 3'-extension of the THD primer by the polymerase activity of the nucleic acid polymerase. A signal indicative of the presence of the target nucleic acid is obtained.

Detection of signal by predetermined time interval

Real-time signal detection

DPO: Dual Priming Oligonucleotide

Fig. 2A

Real-time signal amplification

A. Hybridization

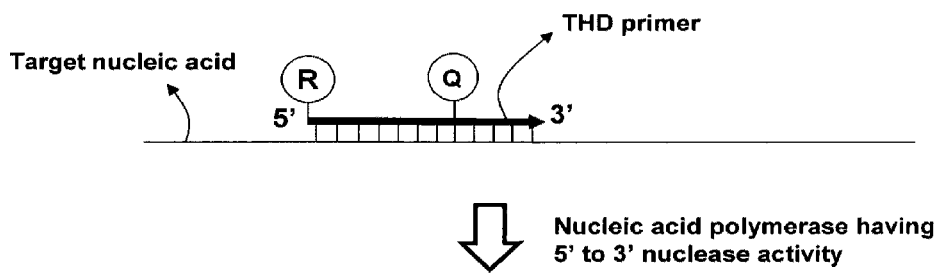

Nucleic acid polymerase having 5' to 3' nuclease activity

B. Signal generation by 5'-cleavage & 3'-extension of the THD primer

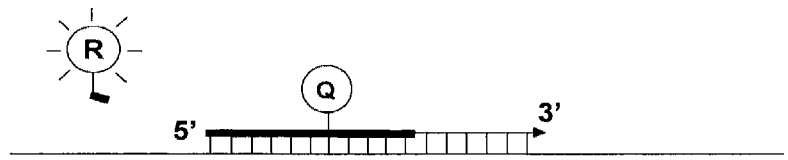

5'-cleavage of the THD primer by the 5' to 3' nuclease activity of the nucleic acid polymerase and 3'-extension of the THD primer by the polymerase activity of the nucleic acid polymerase. A signal indicative of the presence of the target nucleic acid is obtained.

Repetition of denaturation, hybridization, cleavage and extension

Real-time signal amplification (R) : Reporter molecule          (Q) : Quencher molecule

Fig. 2B

Real-time signal amplification

A. Hybridization

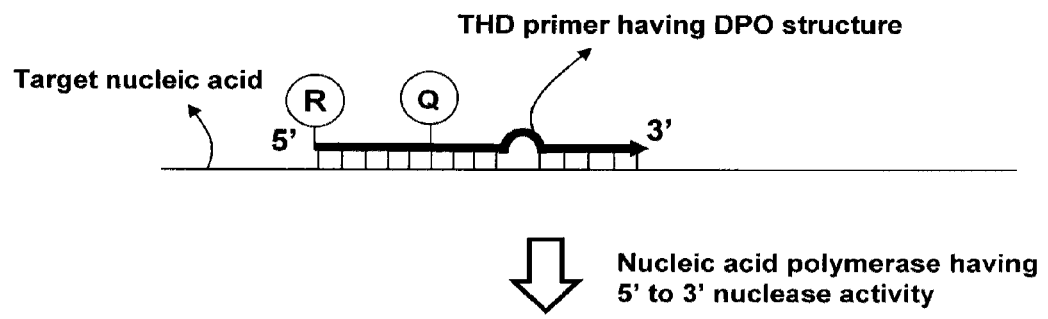

THD primer having DPO structure

Target nucleic acid

⬇ Nucleic acid polymerase having 5' to 3' nuclease activity

B. Signal generation by 5'-cleavage & 3'-extension of the THD primer

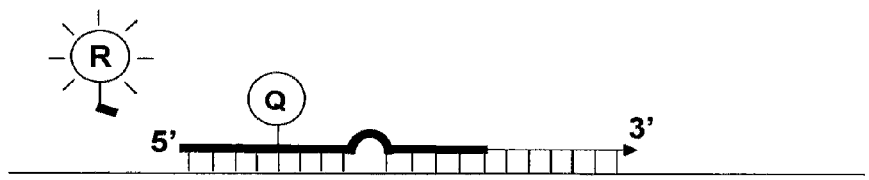

5'-cleavage of the THD primer by the 5' to 3' nuclease activity of the nucleic acid polymerase and 3'-extension of the THD primer by the polymerase activity of the nucleic acid polymerase. A signal indicative of the presence of the target nucleic acid is obtained.

⬇ Repetition of denaturation, hybridization, cleavage and extension

Real-time signal amplification

 : Reporter molecule      : Quencher molecule

DPO: Dual Priming Oligonucleotide

Fig. 3A

Real-time PCR using the THD primer

A. Hybridization

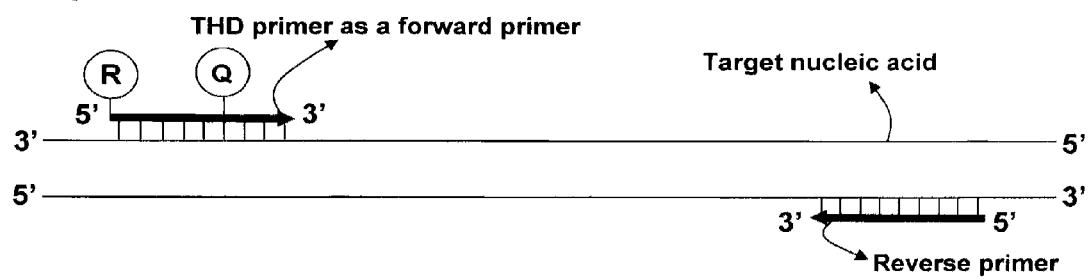

B. Signal generation by 5'-cleavage & 3'-extension of the THD primer

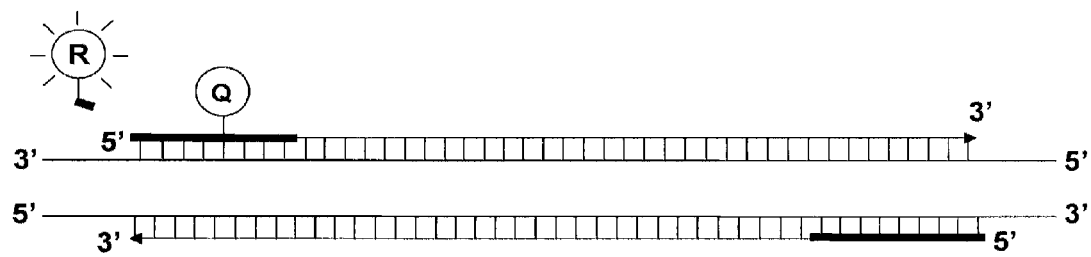

5'-cleavage of the THD primer by the 5' to 3' nuclease activity of the nucleic acid polymerase and 3'-extension of the THD primer by the polymerase activity of the nucleic acid polymerase. A signal indicative of the presence of the target nucleic acid is obtained.

 Repetition of denaturation, hybridization, cleavage and extension

Real-time amplification of signal and target nucleic acids

 : Reporter molecule      : Quencher molecule

Fig. 3B

Real-time PCR using the THD primer

A. Hybridization

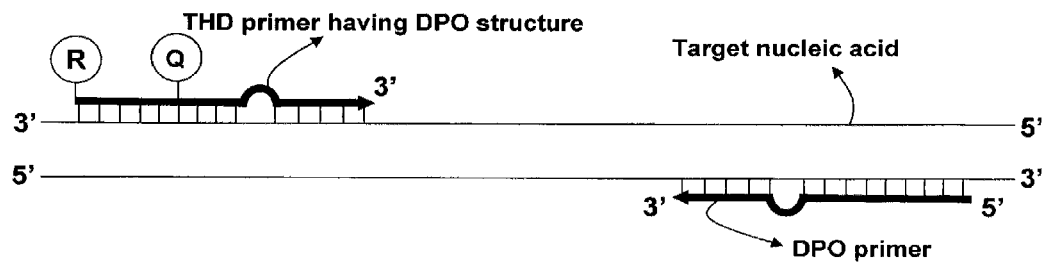

B. Signal generation by 5'-cleavage & 3'-extension of the THD primer

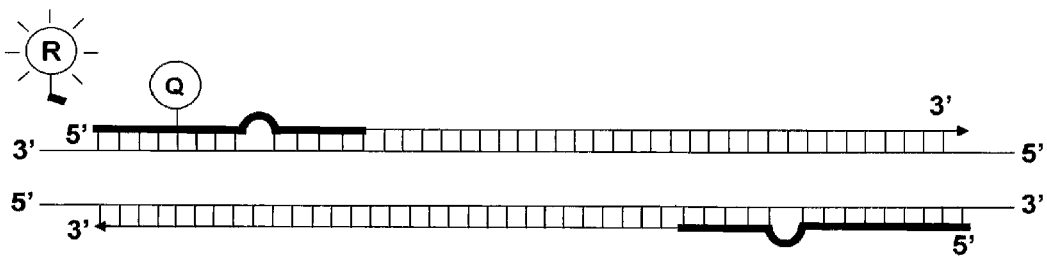

5'-cleavage of the THD primer by the 5' to 3' nuclease activity of the nucleic acid polymerase and 3'-extension of the THD primer by the polymerase activity of the nucleic acid polymerase. A signal indicative of the presence of the target nucleic acid is obtained.

⇩ Repetition of denaturation, hybridization, cleavage and extension

Real-time amplification of signal and target nucleic acids

(R) : Reporter molecule          (Q) : Quencher molecule

DPO: Dual Priming Oligonucleotide

Fig. 4A
Real-time PCR using different combinations of the THD primer
A. Combination of the THD primer as a forward primer
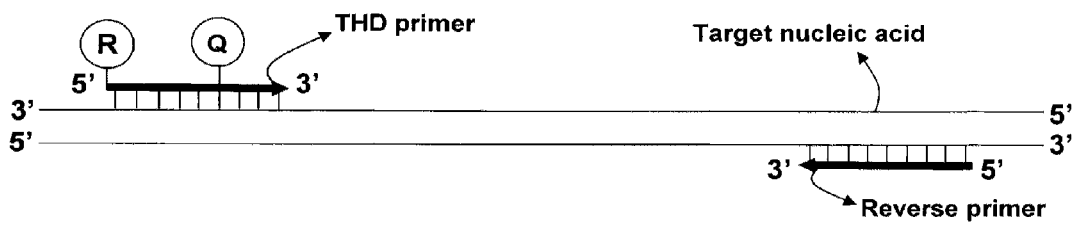
B. Combination of the THD primer as a reverse primer
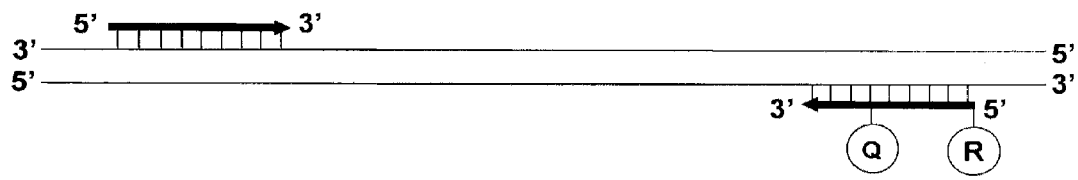
C. Combination of the THD primers as forward and reverse primers
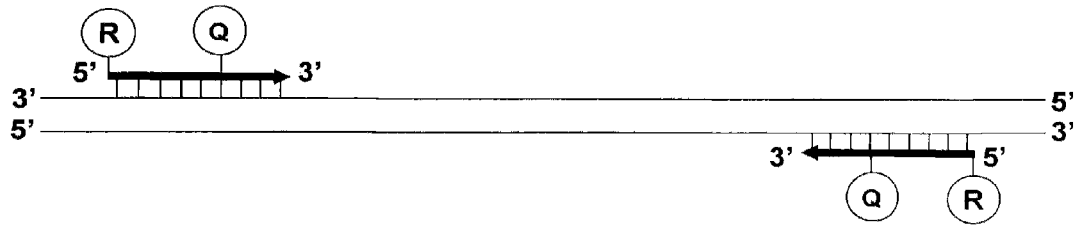

Fig. 4B
Real-time PCR using different combinations of the THD primer
A. Combination of the THD primer as a forward primer with a probe
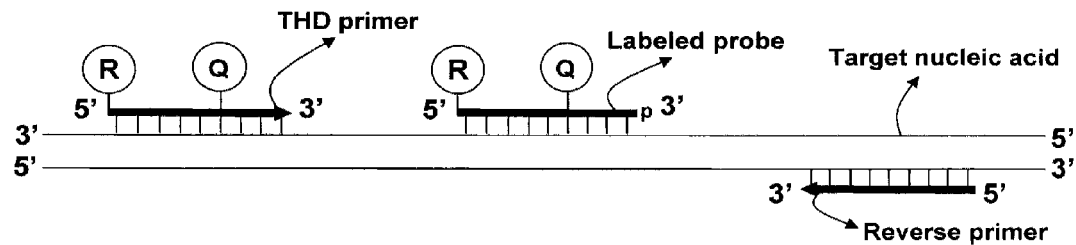
B. Combination of the THD primer as a reverse primer with a probe
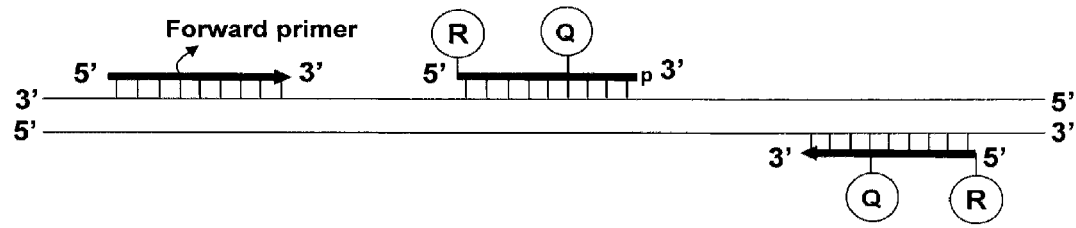
C. Combination of the THD primers as forward/reverse primers with a probe
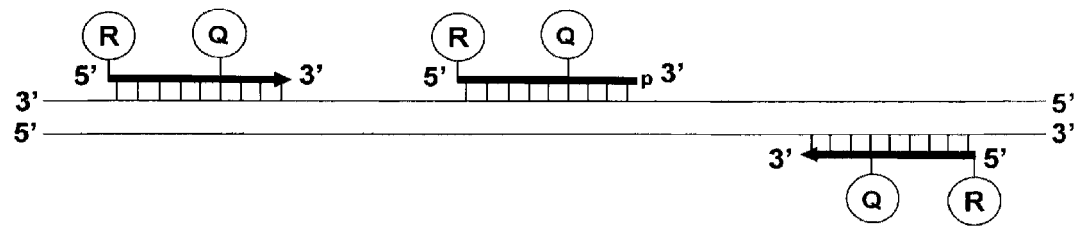
(R) : Reporter molecule  (Q) : Quencher molecule
P: Phosphate for blocking 3'-extension of the probe

Fig. 4C
Real-time PCR using different combinations of the THD primer
A. Combination of the THD primers as forward and upstream primers
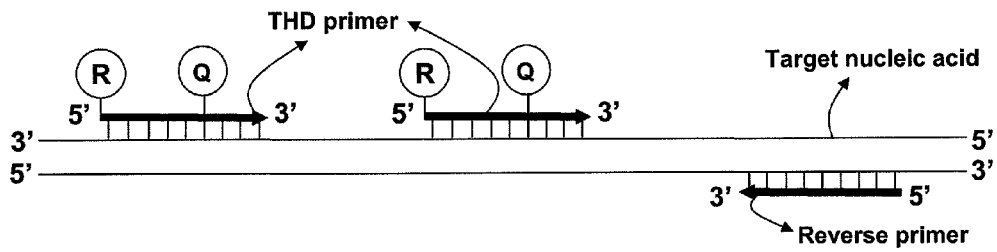
B. Combination of the THD primers as forward and reverse primers
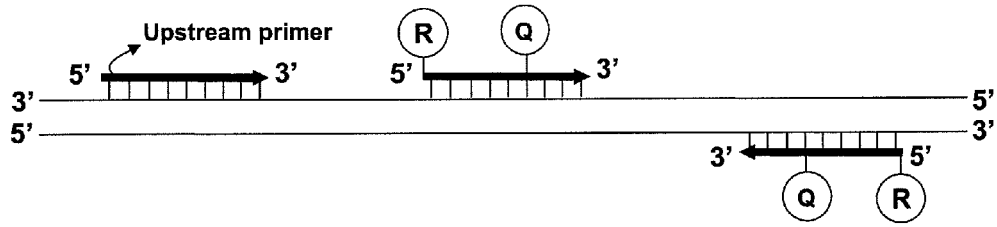
C. Combination of the THD primers as forward, upstream and reverse primers
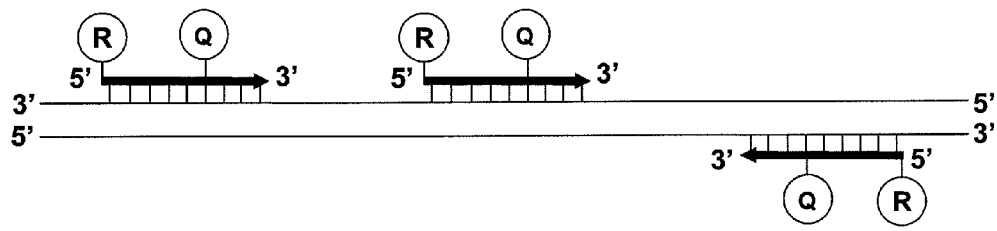
D. Combination of the THD primer as a forward primer
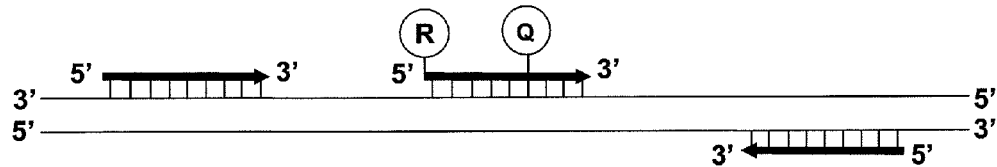
(R) : Reporter molecule      (Q) : Quencher molecule

Fig. 4D
Real-time PCR using different combinations of the THD primer
A. Combination of the THD primer as a forward primer with an internal primer
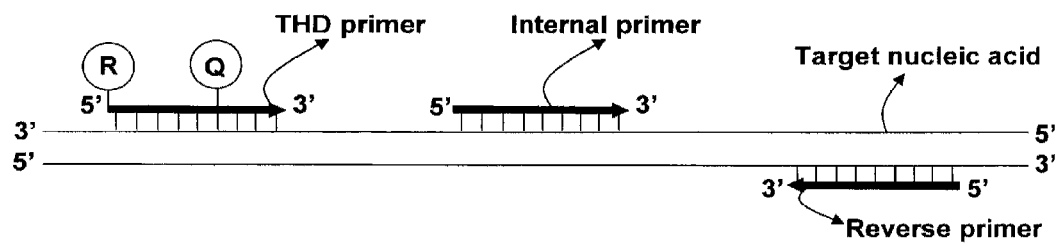
B. Combination of the THD primer as a reverse primer with an internal primer
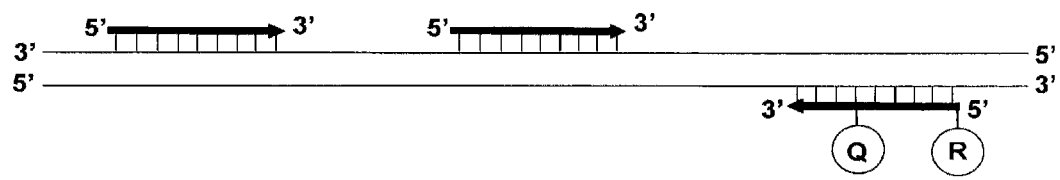
C. Combination of the THD primers as forward/reverse primers with an internal primer
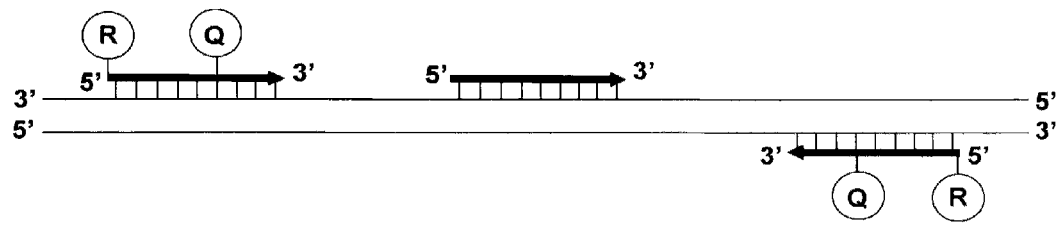
 : Reporter molecule   : Quencher molecule

| No. | Template[1] | THD Primer[2] | Temperature | Ct value |
|---|---|---|---|---|
| 1 | - | + | 55℃ | - |
| 2 | + | + | 55℃ | 5.32 |
| 3 | - | + | 65℃ | - |
| 4 | + | + | 65℃ | 5.09 |

[1] Template is a synthetic oligonucleotide for S. aureus gene.
[2] THD primer has a conventional structure with a dual label.

| No. | Enzyme | Template[1] | THD Primer[2] | Con. of dNTPs | Ct value |
|---|---|---|---|---|---|
| 1 | - | + | + | - | - |
| 2 | + | - | + | - | - |
| 3 | + | + | + | 500 µM | 3.33 |
| 4 | + | + | + | 200 µM | 1.71 |
| 5 | + | + | + | 20 µM | 1.38 |
| 6 | + | + | + | - | 2.23 |

[1] Template is a synthetic oligonucleotide for *S. aureus* gene.
[2] THD primer has a conventional structure with a dual label.

Fig. 7A

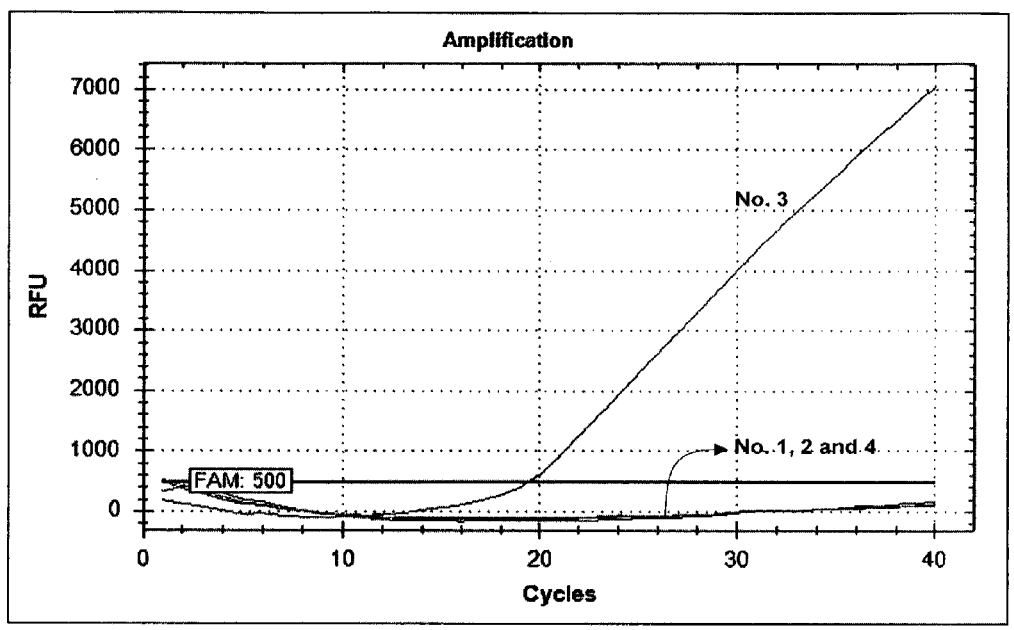

| No. | Template[1] | Forward Primer | Probe[3] | Reverse primer | Ct value |
|---|---|---|---|---|---|
| 1 | + | - | + | Primer[4] | - |
| 2 | - | - | + | Primer | - |
| 3 | + | THD[2] | - | Primer | 19.45 |
| 4 | - | THD | - | Primer | - |

[1] Template is a genomic DNA of S. pneumoniae.
[2] THD represents a THD primer having a conventional structure with a dual label.
[3] Probe has a conventional structure with a dual label and a phosphate at its 3'-end.
[4] Primer presents a primer having a conventional structure without a label.

M: DNA size marker
Lanes 1 and 3: probe
Lanes 2 and 4: THD primer

Fig. 8A

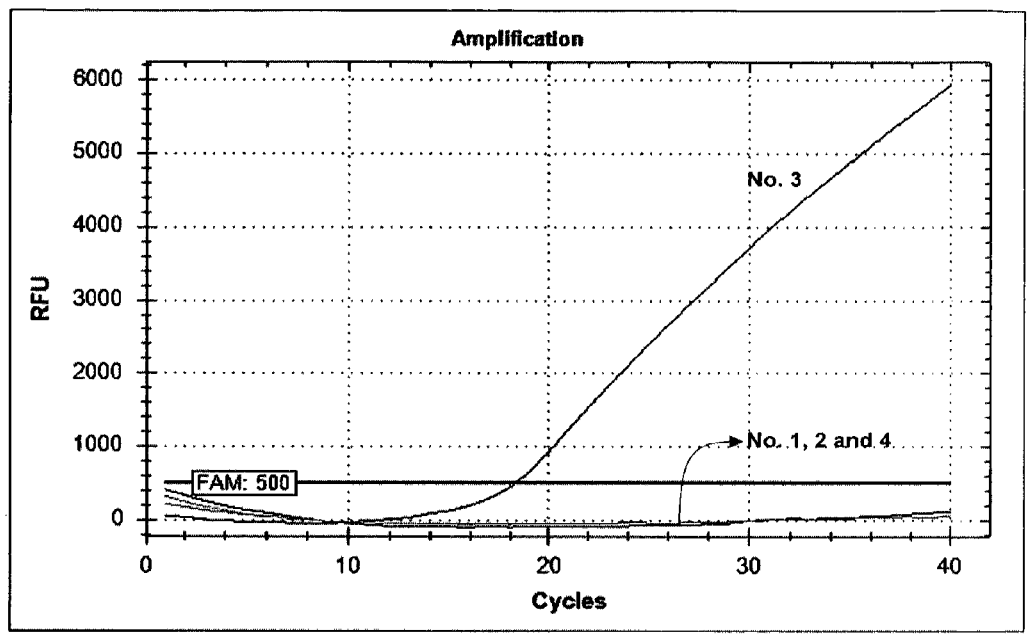

| No. | Template[1] | Forward Primer | Probe[3] | Reverse primer | Ct value |
|---|---|---|---|---|---|
| 1 | + | - | + | Primer[4] | - |
| 2 | - | - | + | Primer | - |
| 3 | + | THD[2] | - | Primer | 18.27 |
| 4 | - | THD | - | Primer | - |

[1] Template is a genomic DNA of *N. meningitidis*.

[2] THD represents a THD primer having a conventional structure with a dual label.

[3] Probe has a conventional structure with a dual label and a phosphate at its 3'-end.

[4] Primer presents a primer having a conventional structure without a label.

M: DNA size marker
Lanes 1 and 3: probe
Lanes 2 and 4: THD primer

| No. | Template[1] | Forward Primer | Reverse primer | Ct value |
|---|---|---|---|---|
| 1 | SP | THD[2] | Primer[3] | 23.91 |
| 2 | NG | THD | Primer | - |
| 3 | NM | THD | Primer | - |
| 4 | - | THD | Primer | - |

[1] Template is a genomic DNA of *S. pneumoniae* (SP), *N. gonorrhoeae* (NG) or *N. meningitidis* (NM).

[2] THD represents a THD primer having a conventional structure with a dual label.

[3] Primer presents a primer having a conventional structure without a label.

| No. | Template[1] | Forward Primer | Reverse primer | Ct value |
|---|---|---|---|---|
| 1 | NM | THD[2] | Primer[3] | 21.60 |
| 2 | NG | THD | Primer | - |
| 3 | SP | THD | Primer | - |
| 4 | - | THD | Primer | - |

[1] Template is a genomic DNA of *N. meningitidis* (NM), *N. gonorrhoeae* (NG) or *S. pneumoniae* (SP).
[2] THD represents a THD primer having a DPO structure with a dual label.
[3] Primer presents a primer having a conventional structure without a label.

| No. | Template[1] | Forward Primer | Reverse primer | Ct value |
|---|---|---|---|---|
| 1 | 10 ng | THD[2] | Primer[3] | 18.98 |
| 2 | 1 ng | THD | Primer | 22.62 |
| 3 | 100 pg | THD | Primer | 26.27 |
| 4 | 10 pg | THD | Primer | 29.96 |
| 5 | 1 pg | THD | Primer | 32.65 |
| 6 | 0.1 pg | THD | Primer | 37.65 |
| 7 | - | THD | Primer | - |

[1] Template is a genomic DNA of *S. pneumoniae*.

[2] THD represents a THD primer having a conventional structure with a dual label.

[3] Primer presents a primer having a conventional structure without a label.

| No. | Template[1] | Forward Primer | Reverse primer | Ct value |
|---|---|---|---|---|
| 1 | 10 ng | THD[2] | Primer[3] | 18.09 |
| 2 | 1 ng | THD | Primer | 21.60 |
| 3 | 100 pg | THD | Primer | 24.93 |
| 4 | 10 pg | THD | Primer | 27.90 |
| 5 | 1 pg | THD | Primer | 31.67 |
| 6 | 0.1 pg | THD | Primer | 35.59 |
| 7 | - | THD | Primer | - |

[1] Template is a genomic DNA of *N. meningitidis*.

[2] THD represents a THD primer having a DPO structure with a dual label.

[3] Primer presents a primer having a conventional structure without a label.

| No. | Template[1] | Forward Primer | Reverse primer | Ct value |
|---|---|---|---|---|
| 1 | SP | THD[2] | Primer[3] | 2.57 |
| 2 | NG | THD | Primer | - |
| 3 | NM | THD | Primer | - |
| 4 | - | THD | Primer | - |

[1] Template is a genomic DNA of *S. pneumoniae* (SP), *N. gonorrhoeae* (NG) or *N. meningitidis* (NM).

[2] THD represents a THD primer having a conventional structure with a dual label.

[3] Primer presents a primer having a conventional structure without a label.

Fig. 14

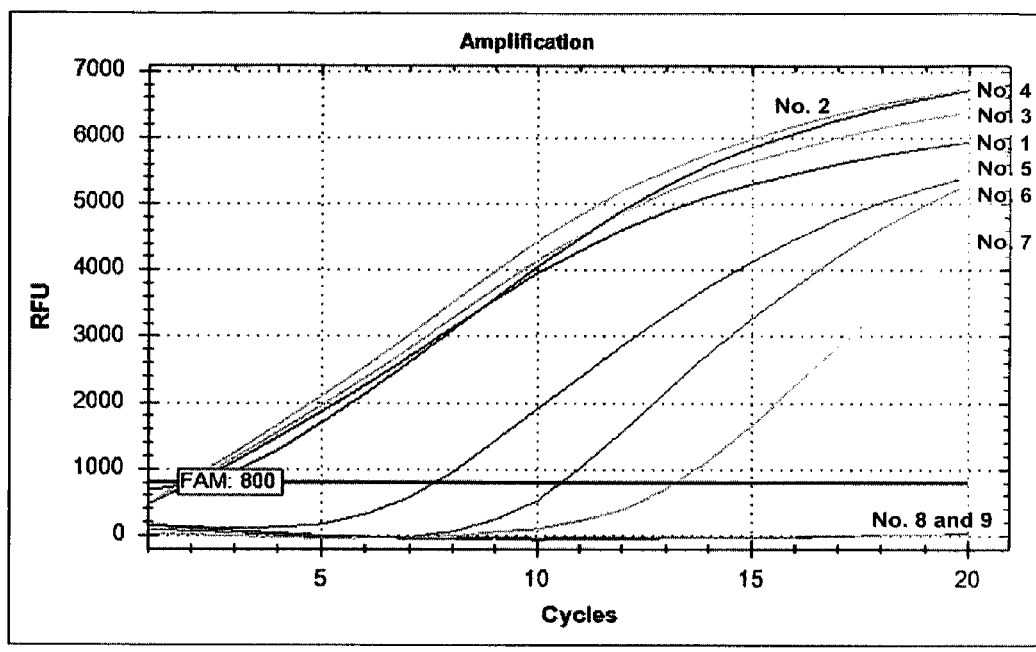

| No. | Template[1] | Forward Primer | Reverse primer | Ct value |
|---|---|---|---|---|
| 1 | 10 ng | THD[2] | Primer[3] | 2.09 |
| 2 | 1 ng | THD | Primer | 1.85 |
| 3 | 100 pg | THD | Primer | 2.01 |
| 4 | 10 pg | THD | Primer | 2.18 |
| 5 | 1 pg | THD | Primer | 7.59 |
| 6 | 100 fg | THD | Primer | 10.55 |
| 7 | 10 fg | THD | Primer | 13.24 |
| 8 | 1 fg | THD | Primer | - |
| 9 | - | THD | Primer | - |

[1] Template is a genomic DNA of S. pneumoniae.

[2] THD represents a THD primer having a conventional structure with a dual label.

[3] Primer presents a primer having a conventional structure without a label.

| No. | Template[1] | Forward primer | Reverse primer | Ct value |
|---|---|---|---|---|
| 1 | + | THD[2] | Primer | 27.93 |
| 2 | + | Primer[3] | THD | 26.90 |
| 3 | + | THD | THD | 26.72 |

[1] Template is a genomic DNA of *N. gonorrhoeae*.

[2] THD represents a THD primer having a DPO structure with a dual label.

[3] Primer represents a primer having a DPO structure without a label.

| No. | Template[1] | Forward primer | Internal probe[4] | Reverse primer | Ct value |
|---|---|---|---|---|---|
| 1 | + | THD[2] | + | Primer | 26.63 |
| 2 | + | Primer[3] | + | THD | 25.88 |
| 3 | + | THD | + | THD | 25.10 |

[1] Template is a genomic DNA of *N. gonorrhoeae*.
[2] THD represents a THD primer having a DPO structure with a dual label.
[3] Primer represents a primer having a DPO structure without a label.
[4] Internal probe has a conventional structure with a dual label.

Fig. 17

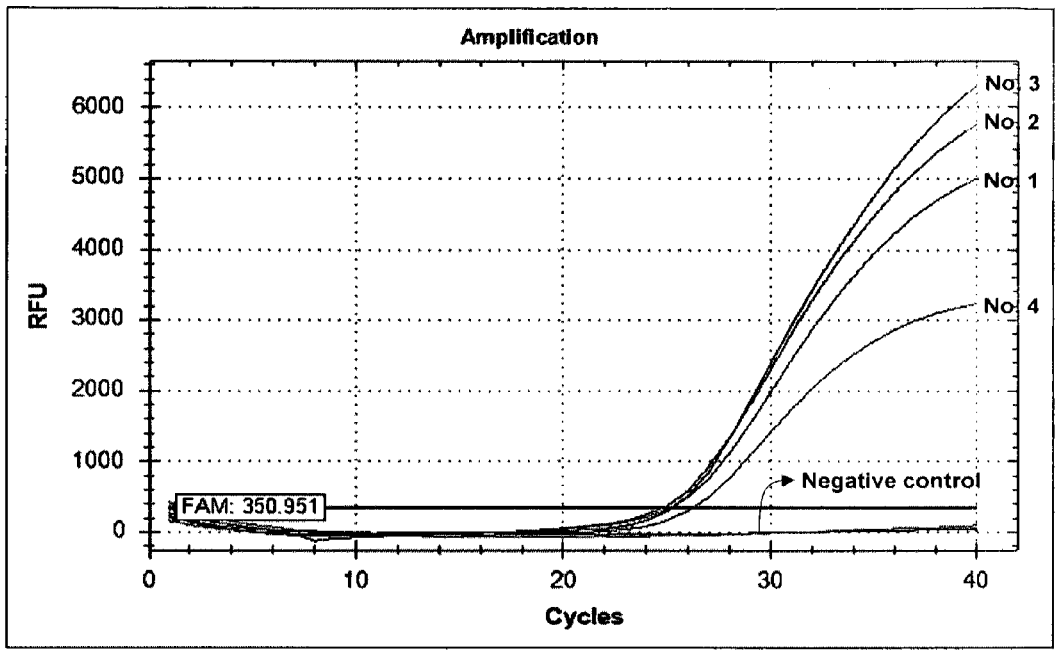

| No. | Template[1] | Upstream primer[2] | Forward primer[3] | Reverse primer[4] | Ct value |
|---|---|---|---|---|---|
| 1 | + | THD[5] | THD | Primer | 25.16 |
| 2 | + | Primer[6] | THD | THD | 24.81 |
| 3 | + | THD | THD | THD | 25.25 |
| 4 | + | Primer | THD | Primer | 26.25 |

[1] Template is a genomic DNA of *N. gonorrhoeae*.

[2],[4] Upstream and reverse primers have a DPO structure.

[3] Forward primer has a conventional structure.

[5] THD represents a THD primer having a dual label.

[6] Primer represents a primer having a DPO structure without a label.

| No. | Template[1] | Forward primer | Internal primer[4] | Reverse primer | Ct value |
|---|---|---|---|---|---|
| 1 | + | THD[2] | + | Primer | 28.89 |
| 2 | + | Primer[3] | + | THD | 26.75 |
| 3 | + | THD | + | THD | 25.55 |

[1] Template is a genomic DNA of *N. gonorrhoeae*.
[2] THD represents a THD primer having a DPO structure with a dual label.
[3] Primer represents a primer having a DPO structure without a label.
[4] Internal primer has a conventional structure without a label.

Fig. 19

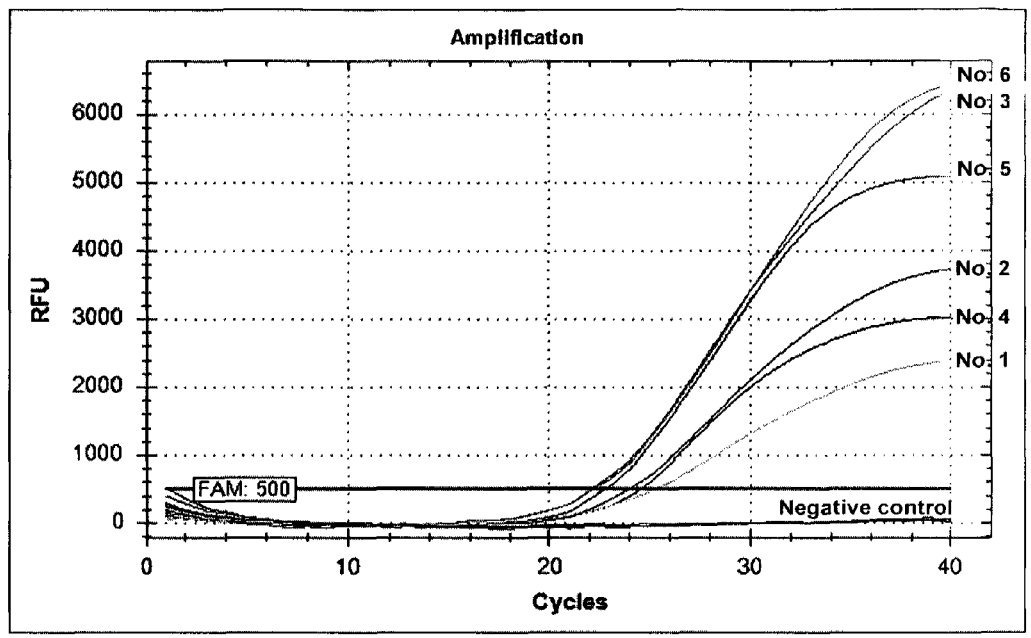

| No. | Template[1] | Forward primer | Internal primer[4] | Internal probe[5] | Reverse primer | Ct value |
|---|---|---|---|---|---|---|
| 1 | + | THD[2] | - | - | Primer | 25.25 |
| 2 | + | Primer[3] | - | - | THD | 23.92 |
| 3 | + | THD | - | - | THD | 22.06 |
| 4 | + | Primer | - | + | Primer | 24.49 |
| 5 | + | Primer | + | - | THD | 22.73 |
| 6 | + | THD | + | - | THD | 22.14 |

[1] Template is a genomic DNA of *N. gonorrhoeae*.

[2] THD represents a THD primer having DPO structure with a dual label.

[3] Primer represents a primer having a DPO structure without a label.

[4] Internal primer has a conventional structure without a label.

[5] Internal probe has a conventional structure with a dual label.

SEQUENCE LISTING

<160> NUMBER OF SEQ ID NOS: 17

<210> SEQ ID NO 1
<211> LENGTH: 200
<212> TYPE: DNA
<213> ORGANISM: Artificial Sequence
<220> FEATURE:
<223> OTHER INFORMATION: Synthetic construct; SA-Tem primer

<400> SEQUENCE: 1
gccaataaaa ctaggaggaa atttaaatgt tagaatttga acaaggatttt aatcatttag    60 cgactttaaa ggtcattggt gtaggtggtg gcggtaacaa cgccgtaaac cgaatgattg   120
accacggaat gaataatgtt gaatttatcg ctatcaacac agacggtcaa gctttaaact   180
tatctaaagc tgaatctaaa                                               200

<210> SEQ ID NO 2
<211> LENGTH: 24
<212> TYPE: DNA
<213> ORGANISM: Artificial Sequence
<220> FEATURE:
<223> OTHER INFORMATION: Synthetic construct; SA-THD primer

<400> SEQUENCE: 2
cattccgtgg tcaatcattc ggtt                                           24

<210> SEQ ID NO 3
<211> LENGTH: 20
<212> TYPE: DNA
<213> ORGANISM: Artificial Sequence
<220> FEATURE:
<223> OTHER INFORMATION: Synthetic construct; SP-P1 primer

<400> SEQUENCE: 3
ttgaccactt cgctatttcc                                              20

<210> SEQ ID NO 4
<211> LENGTH: 25
<212> TYPE: DNA
<213> ORGANISM: Artificial Sequence
<220> FEATURE:
<223> OTHER INFORMATION: Synthetic construct; SP-THD primer

<400> SEQUENCE: 4
tccttcaaac tgtggatttg ggtgt                                        25

<210> SEQ ID NO 5
<211> LENGTH: 25
<212> TYPE: DNA
<213> ORGANISM: Artificial Sequence
<220> FEATURE:
<223> OTHER INFORMATION: Synthetic construct; SP-Probe

<400> SEQUENCE: 5
tccttcaaac tgtggatttg ggtgt                                        25

<210> SEQ ID NO 6
<211> LENGTH: 19
<212> TYPE: DNA
<213> ORGANISM: Artificial Sequence
<220> FEATURE:
<223> OTHER INFORMATION: Synthetic construct; SP-P2 primer

<400> SEQUENCE: 6
ggtttccgta cagccttga                                               19

<210> SEQ ID NO 7
<211> LENGTH: 35
<212> TYPE: DNA
<213> ORGANISM: Artificial Sequence
<220> FEATURE:
<223> OTHER INFORMATION: Synthetic construct; NM-THD1 primer
<220> FEATURE:
<221> NAME/KEY: misc_feature
<222> LOCATION: (21)..(25)
<223> OTHER INFORMATION: n denotes deoxyinosine

<400> SEQUENCE: 7
ccataacctt gagcaatcca nnnnncctga cgttc                             35

<210> SEQ ID NO 8
<211> LENGTH: 22
<212> TYPE: DNA
<213> ORGANISM: Artificial Sequence
<220> FEATURE:
<223> OTHER INFORMATION: Synthetic construct; NM-THD2 primer

<400> SEQUENCE: 8
tccaccaatg gcgtatagcg ga                                           22

<210> SEQ ID NO 9
<211> LENGTH: 22
<212> TYPE: DNA
<213> ORGANISM: Artificial Sequence
<220> FEATURE:
<223> OTHER INFORMATION: Synthetic construct; NM-Probe

<400> SEQUENCE: 9
tccaccaatg gcgtatagcg ga                                           22

```
<210> SEQ ID NO 10
<211> LENGTH: 22
<212> TYPE: DNA
<213> ORGANISM: Artificial Sequence
<220> FEATURE:
<223> OTHER INFORMATION: Synthetic construct; NM-P1 primer

<400> SEQUENCE: 10
ccaatcccta tacctttacg tc                                              22

<210> SEQ ID NO 11
<211> LENGTH: 37
<212> TYPE: DNA
<213> ORGANISM: Artificial Sequence
<220> FEATURE:
<223> OTHER INFORMATION: Synthetic construct; NG-P1 primer
<220> FEATURE:
<221> NAME/KEY: misc_feature
<222> LOCATION: (22)..(26)
<223> OTHER INFORMATION: n denotes deoxyinosine

<400> SEQUENCE: 11
caatggatcg gtatcactcg cnnnnncgag caagaac                              37

<210> SEQ ID NO 12
<211> LENGTH: 37
<212> TYPE: DNA
<213> ORGANISM: Artificial Sequence
<220> FEATURE:
<223> OTHER INFORMATION: Synthetic construct; NG-THD1 primer
<220> FEATURE:
<221> NAME/KEY: misc_feature
<222> LOCATION: (22)..(26)
<223> OTHER INFORMATION: n denotes deoxyinosine

<400> SEQUENCE: 12
caatggatcg gtatcactcg cnnnnncgag caagaac                              37

<210> SEQ ID NO 13
<211> LENGTH: 24
<212> TYPE: DNA
<213> ORGANISM: Artificial Sequence
<220> FEATURE:
<223> OTHER INFORMATION: Synthetic construct; NG-P2 primer

<400> SEQUENCE: 13
attggcgtgt ttcgcatatt taag                                            24

<210> SEQ ID NO 14
<211> LENGTH: 24
<212> TYPE: DNA
<213> ORGANISM: Artificial Sequence
<220> FEATURE:
<223> OTHER INFORMATION: Synthetic construct; NG-THD2 primer

<400> SEQUENCE: 14
attggcgtgt ttcgcatatt taag                                            24

<210> SEQ ID NO 15
<211> LENGTH: 24
<212> TYPE: DNA
<213> ORGANISM: Artificial Sequence
<220> FEATURE:
<223> OTHER INFORMATION: Synthetic construct; NG-Probe
```

-continued

```
<400> SEQUENCE: 15
attggcgtgt ttcgcatatt taag                                              24

<210> SEQ ID NO 16
<211> LENGTH: 37
<212> TYPE: DNA
<213> ORGANISM: Artificial Sequence
<220> FEATURE:
<223> OTHER INFORMATION: Synthetic construct; NG-P3 primer
<220> FEATURE:
<221> NAME/KEY: misc_feature
<222> LOCATION: (22)..(26)
<223> OTHER INFORMATION: n denotes deoxyinosine

<400> SEQUENCE: 16
tacgcctgct actttcacgc tnnnnngtaa tcagatg                                37

<210> SEQ ID NO 17
<211> LENGTH: 37
<212> TYPE: DNA
<213> ORGANISM: Artificial Sequence
<220> FEATURE:
<223> OTHER INFORMATION: Synthetic construct; NG-THD3 primer
<220> FEATURE:
<221> NAME/KEY: misc_feature
<222> LOCATION: (22)..(26)
<223> OTHER INFORMATION: n denotes deoxyinosine

<400> SEQUENCE: 17
tacgcctgct actttcacgc tnnnnngtaa tcagatg                                37
```

DETECTION OF TARGET NUCLEIC ACID USING A TARGET HYBRIDIZATION AND DETECTION PRIMER

CROSS REFERENCE TO RELATED APPLICATIONS

This application claims the priority of PCT/KR2009/007064, filed on Nov. 28, 2009, which claims the benefit of priority to Korean Application No. 10-2009-0107262, filed on Nov. 7, 2009, the entire contents of each of which are hereby incorporated in total by reference.

SEQUENCE LISTING

This application incorporates by reference the Sequence Listing contained in an ASCII text file named "361406_00011_ST25.txt" submitted via EFS-Web. The text file was created on May 4, 2012, and is 4.34 kb in size.

BACKGROUND OF THE INVENTION

1. Field of the Invention

The present invention relates to the detection of a target nucleic acid sequence using a target hybridization and detection primer (THD primer).

2. Description of the Related Art

A target nucleic acid amplification process is prevalently involved in most of technologies for detecting target nucleic acid sequences. Nucleic acid amplification is a pivotal process for a wide variety of methods in molecular biology, such that various amplification methods have been proposed. For example, Miller, H. I. et al. (WO 89/06700) amplified a nucleic acid sequence based on the hybridization of a promoter/primer sequence to a target single-stranded DNA ("ssDNA") followed by transcription of many RNA copies of the sequence. Other known nucleic acid amplification procedures include transcription-based amplification systems (Kwoh, D. et al., *Proc. Natl. Acad. Sci. U.S.A.*, 86:1173 (1989); and Gingeras T. R. et al., WO 88/10315).

The most predominant process for nucleic acid amplification known as polymerase chain reaction (hereinafter referred to as "PCR") is based on repeated cycles of denaturation of double-stranded DNA, followed by oligonucleotide primer annealing to the DNA template, and primer extension by a DNA polymerase (Mullis et al. U.S. Pat. Nos. 4,683,195, 4,683,202, and 4,800,159; Saiki et al., (1985) Science 230, 1350-1354).

PCR-based techniques have been widely used not only for amplification of a target DNA sequence, but also for scientific applications or methods in the fields of biological and medical research, such as reverse transcriptase PCR(RT-PCR), differential display PCR (DD-PCR), cloning of known or unknown genes by PCR, rapid amplification of cDNA ends (RACE), arbitrary priming PCR (AP-PCR), multiplex PCR, SNP genome typing, and PCR-based genomic analysis (McPherson and Moller, (2000) PCR. BIOS Scientific Publishers, Springer-Verlag New York Berlin Heidelberg, NY).

In the meantime, methods for detecting target nucleic acids based on nucleic acid amplification proposed up to now are summarized as follows:

1. Post-PCR Detection Method

The post-PCR method which is typically heterogeneous involves nucleic acid amplification and thereafter detection of amplified products for analyzing target nucleic acid sequence. The conventional post-PCR detection method requires the amplified products to be separated either on the basis of a size differential, which is commonly achieved through the use of gel electrophoresis, or by the immobilization of the product. However, the separation process causes serious problems such as carry over contamination and low-throughput.

2. Real-Time Detection Methods

To overcome problems of the post-PCR method, a real-time PCR method was suggested to detect amplified products in real-time manner and be free from contaminants, making it possible to quantitatively analyze target nucleic acid sequences.

2.1 Methods Using Hybridization and Extension Reactions 2.1.1 Sunrise Primer Method This method uses sunrise primers which form hairpin loops at their 5' ends to bring a fluorophore and quencher pair together, thus ensuring low fluorescence. When these primers have been incorporated into a PCR product, the tails become double stranded and the hairpin is unraveled causing the fluorescence to increase (Nazarenko et al, 2516-2521 Nucleic Acids Research, 1997, v.25 no.12, and U.S. Pat. No. 6,117,635). However, the sunrise primer method is very inconvenient in that primers are intricately designed to contain a complementary sequence to target nucleic acid sequences and a sequence capable of forming hairpin loops at their 5' ends.

2.1.2 Tailed Primer Method (Scorpion Primer Method)

This method uses a tailed primer (scorpion primer) and an integrated signaling system. The primer has a template binding region and the tail comprising a linker and a target binding region. The target binding region is hybridized with a complementary sequence in an extension product of the primer. Afterwards, this target specific hybridization event is coupled to a signaling system wherein hybridization leads to a detectable change. The linker in the tailed primer prevents polymerase mediated chain copying of the tail region of the primer template (Whitcombe et al, 804-807, Nature Biotechnology v.17 AUGUST 1999 and U.S. Pat. No. 6,326,145). Like the sunrise primer method, this tailed primer also has a difficulty in designing and synthesizing primers due to incorporation of a linker to generate amplicon-dependent signals and a target binding region hybridizable with a primer extension product into a primer.

2.2 Methods Using Hybridization Reactions 2.2.1 Molecular Beacon Method

Molecular beacons contain fluorescent and quenching dyes, but FRET (fluorescence resonance energy transfer) only occurs when the quenching dye is directly adjacent to the fluorescent dye. Molecular beacons are designed to adopt a hairpin structure while free in solution, bringing the both dyes in close proximity. When a molecular beacon hybridizes to a target, fluorescent and quencher dyes are separated. FRET does not occur and fluorescent dye emits light upon irradiation (Indian 3 Med Res 124: 385-398 (2006) and Tyagi et al, Nature Biotechnology v.14 MARCH 1996).

However, there are some drawbacks in the molecular beacon method.

Firstly, the two inverted repeats of the hairpin structure must have complementary counterparts in the target nucleic acid, which in turn requires the presence of inverted repeats in the target as well, a condition that is not generally met.

Secondly, the $T_m$ of the loop portion of the hairpin structure with a complementary nucleic acid sequence and the Tm of the stem portion need to be carefully balanced with respect to the temperature of the assay to allow the specific unfolding of the hairpin probe in the presence of the target without unspecific unfolding.

Lastly, this method demands additional primers for amplifying target nucleic acid sequences.

2.2.2 Hybridization Probe Methods

This method uses four oligonucleotides: two primers and two probes. Hybridization probes have a single label, one with a donor fluorophore and one with an acceptor fluorophore. The sequence of the two probes are selected so that they can hybridize to the target sequences in a head to tail arrangement, bringing the tow dyes very close to each other, allowing fluorescence resonance energy transfer (FRET). The acceptor dye in one of the probes transfers energy, allowing the other one to dissipate fluorescence at a different wavelength. The amount of fluorescence is directly proportional to the amount of target DNA generated during the PCR process (385-398, Indian J Med Res 124, review article Oct. 2006 and 303-308, and Bernad et al, 147-148 Clin Chem 2000; 46).

However, this method is not adoptable to multiplex detection and requires additional primers for amplifying target nucleic acid sequences.

2.3 Methods Using Hybridization and Nuclease Activity 2.3.1 Taqman Probe Method (5' to 3' Nuclease Activity)

TaqMan probes are designed to hybridize to an internal region of a PCR product. During PCR when the polymerase replicates a template on which a TaqMan probe is bound, the 5' exonuclease activity of the polymerase cleaves the probe. This separates the fluorescent and quenching dyes and FRET no longer occurs (385-398, Indian J Med Res 124, review article Oct. 2006 and 303-308, U.S. Pat. No. 5,210,015).

However, this method is limited in the sense that it employs three oligonucleotides (a dual label probe and two primers). This seriously complicates probe design and synthesis, and reaction condition optimization.

2.3.2. Labeled Primer Method (3' to 5' Nuclease Activity)

This method uses a labeled primer deliberately mismatched in at least one nucleotide at the 3' end of the primer. The labeled primer is incubated with a sample under conditions sufficient to allow hybridization and said sample is subsequently exposed to nucleic acid polymerase having a 3' to 5' proofreading activity, thereby releasing said label or part of the label system (U.S. Pat. No. 6,248,526).

However, the mismatch primer should be intricately designed to contain a mismatch nucleotide at its 3'-end. To make matters worse, the mismatch primer is likely to generate false positive signals by the 3' to 5' proofreading activity even when the 3'-end is mismatched to non-target sequences.

As described above, most of conventional target detection methods developed hitherto have intrinsic shortcomings which are considered difficult to overcome.

Accordingly, there is a long-felt need for novel approach to detect target nucleic acid sequences in more technical-, time- and cost-effective manner.

Throughout this application, various patents and publications are referenced, and citations are provided in parentheses. The disclosure of these patents and publications in their entities are hereby incorporated by references into this application in order to more fully describe this invention and the state of the art to which this invention pertains.

SUMMARY OF THE INVENTION

The present inventors have made intensive researches to overcome shortcomings associated with conventional technologies for detection of target nucleic acid sequences. The present inventors have devised new analytic-functional primers with a dual surveillance function, i.e., probing and priming, and have in turn constructed various protocols using the primers for detection of target nucleic acid sequences. As results, we have verified that the new protocols or processes exhibit a plausible performance in detection of target nucleic acid sequences, inter alia, real-time detection, and produce signals indicating a target nucleic acid sequence in much stronger and faster manner.

The key discovery of the present inventors is that when a primer hybridized with a target nucleic acid sequence is contacted to a template-dependent nucleic acid polymerase having a 5' to 3' nuclease activity under conditions for the 5'-cleavage reaction and the 3'-extension reaction of the primer by the template-dependent nucleic acid polymerase, its 3'-end is extended and its 5'-end portion is also cleaved, which is the basis governing the present invention. Based on these findings and discoveries, when a label generating a detectable signal has been incorporated into a primer to generate amplicons in PCR reactions, a signal has been found to generate during real-time PCR reactions. This application has turned out to be more efficient in target detection than existing methods where additional probes or modification of primers are required. The labeled primer of the present invention can not only provide incomparably powerful and flexible tool for effective detection of target nucleic acid sequences, but also make the development process of real-time PCR assays simpler, shorter and more economical.

Accordingly, it is an object of this invention to provide a method for detecting a target nucleic acid sequence from a DNA or a mixture of nucleic acids using a 5'-cleavage reaction and a 3'-extension reaction of a target hybridization and detection primer (THD primer).

It is another object of this invention to provide a method for detecting a target nucleic acid sequence from a DNA or a mixture of nucleic acids using a polymerase chain reaction (PCR) associated with a 5'-cleavage reaction and a 3'-extension reaction of a target hybridization and detection primer (THD primer).

It is further object of this invention to provide a kit for detecting a target nucleic acid sequence from a DNA or a mixture of nucleic acids using a 5'-cleavage reaction and a 3'-extension reaction of a target hybridization and detection primer (THD primer).

Other objects and advantages of the present invention will become apparent from the detailed description to follow taken in conjugation with the appended claims and drawings.

BRIEF DESCRIPTION OF THE DRAWINGS

The basic principles of the present invention are outlined in FIGS. 1-4.

FIG. 1 shows the schematic steps involved in an assay for detecting a target nucleic acid sequence using the 5'-cleavage reaction and the 3'-extension reaction of a THD primer by a template-dependent nucleic acid polymerase having a 5' to 3' nuclease activity. FIG. 1A shows the use of the THD primer having a conventional structure for the detection of a target nucleic acid sequence. FIG. 1B shows the use of the THD primer having a dual priming oligonucleotide (DPO) structure for the primer annealing specificity in the detection of a target nucleic acid sequence.

FIG. 2 shows a schematic representation for a real-time signal amplification assay for detecting a target nucleic acid sequence without the amplification of the target nucleic acid sequence using the 5'-cleavage reaction and the 3'-extension reaction of a THD primer by a template-dependent nucleic acid polymerase having a 5' to 3' nuclease activity. FIG. 2A shows the use of the THD primer having a conventional structure for the detection of a target nucleic acid sequence. FIG. 2B shows the use of the THD primer having a dual priming oligonucleotide (DPO) structure for the primer annealing specificity in the detection of a target nucleic acid sequence.

FIG. 3 shows a schematic representation for the real-time amplification of a target nucleic acid and signal during a real-time PCR using a THD primer of this invention. FIG. 3A shows the use of the THD primer having a conventional structure for a real-time PCR amplification. FIG. 3B shows the use of the THD primer having a dual priming oligonucleotide (DPO) structure for the primer annealing specificity in a real-time PCR amplification.

FIG. 4 shows a schematic representation for a variety of THD primer combinations in a real-time PCR amplification. FIG. 4A shows the use of a THD primer as a forward primer, a reverse primer, or both. FIG. 4B shows the use of a labeled probe combined with a THD primer as a forward primer, a reverse primer, or both. FIG. 4C shows the use of a THD primer as a forward primer combined with an additional THD primer as an upstream primer, a reverse primer or both. FIG. 4D shows the use of an internal primer combined with a THD primer as a forward primer, a reverse primer, or both.

FIG. 7 shows the comparison of a THD primer and a labeled probe in real-time PCR amplification for *Streptococcus pneumoniae* (SP) gene. FIG. 7A shows the results of the real-time PCR amplification.

FIG. 8 shows the comparison of a THD primer and a labeled probe in real-time PCR amplification for *Neisseria meningitides* (NM) gene. FIG. 8A shows the results of the real-time PCR amplification.

FIG. 14 shows the real-time PCR sensitivity for *Streptococcus pneumoniae* (SP) gene using a THD primer as a forward primer in the nested real-time PCR amplification.

FIG. 17 shows the results used a THD primer as a forward primer combined with an additional THD primer as an upstream primer, a reverse primer or both in the real-time PCR amplification for *Neisseria gonorrhoeae* (NG) gene.

FIG. 19 shows the comparison of methods using a THD primer and the TaqMan probe in the real-time PCR amplification for *Neisseria gonorrhoeae* (NG) gene.

DETAILED DESCRIPTION OF THIS INVENTION

Figure 5:
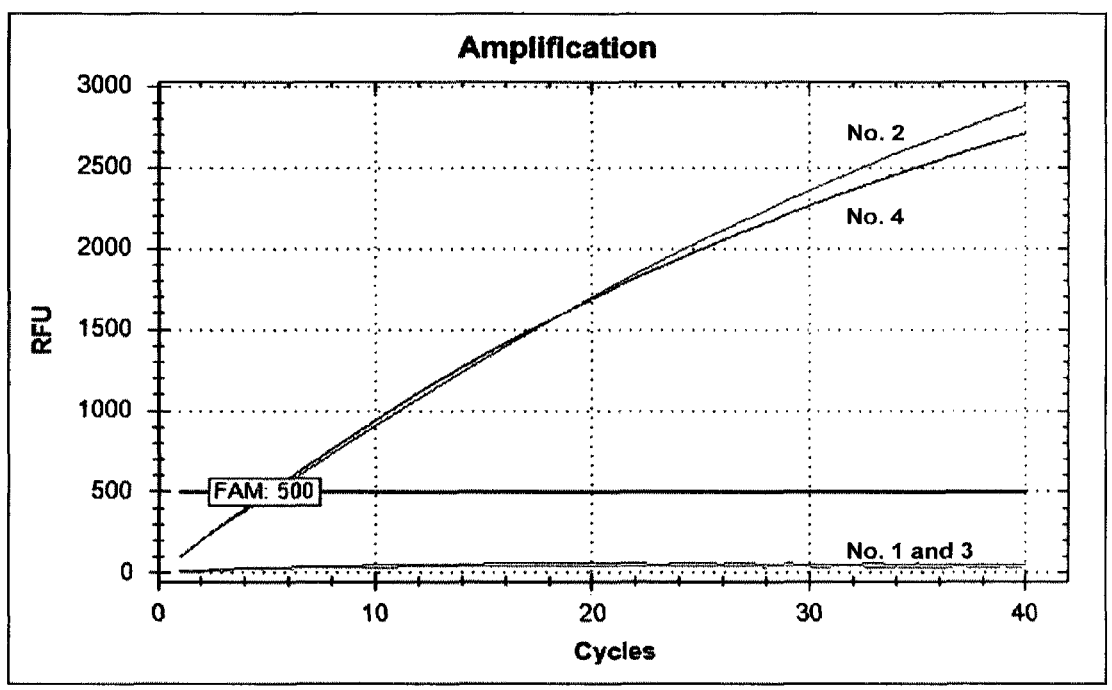
FIG. 5 shows the detection of a target nucleic acid sequence using a THD primer of this invention and Taq DNA polymerase without the repetition of denaturation, hybridization, cleavage and extension at a predetermined time interval.

The present invention is directed to a novel method for detecting a target nucleic acid sequence using a primer with a label and a 5' to 3' nuclease activity of a template-dependent nucleic acid polymerase. Specifically, the present invention relates to a plausible proposal to detect a target nucleic acid sequence in a real-time fashion.

The labeled primer called a target hybridization and detection primer (THD primer) is hybridized with a target nucleic acid sequence, and then extended to synthesize a complementary sequence of the target nucleic acid sequence and cleaved to release the label from the primer, thereby generating a signal indicative of the presence of the target nucleic acid sequence. In other words, the THD primer undergoes the 5'-cleavage reaction and the 3'-extension reaction.

The present inventors have found that when the THD primer having an interactive label system containing a fluorescent reporter molecule and a quencher molecule is hybridized with a target nucleic acid sequence and then incubated with a template-dependent nucleic acid polymerase having a 5' to 3' nuclease activity, the label (labeled fragment) is released from the THD primer to generate a signal indicating the presence of the target nucleic acid sequence.

Furthermore, the present inventors have discovered that the extension at the 3'-end of the THD primer ensures much less variation in signal intensity over change of reaction temperature, leading us to reason that more reliable and stable signal results could be obtained by the extension at the 3'-end of the THD primer with little or no signal influence upon reaction temperature change. In addition to this, the THD primer may be also served as amplification primers in the present method, such that the target nucleic acid sequence is amplified along with signal amplification.

In accordance with the present invention, the target nucleic acid sequences could be detected in a real-time manner with dramatically enhanced efficiency and reliability using the labeled primers and the 5' to 3' nuclease activity of the template-dependent nucleic acid polymerase. To our best knowledge, these scientific findings and technological strategies are first proposed by the present inventors.

The 3'-extension reaction is responsible for the stabilization of hybridization of the THD primer with the target nucleic acid sequence and much less variation in signal intensity over change of reaction temperature.

Based on our findings described above, a general procedure of the present invention is proposed as follows: A primer labeled by conventional procedures and a template-dependent nucleic acid polymerase having a 5' to 3' nuclease activity are incubated with a sample containing a target nucleic acid sequence, such that a 3'-extension reaction and a 5'-cleavage reaction of the primer are induced to release a label from the primer, finally yielding a signal indicative of the presence of the target nucleic acid sequence.

In accordance with the present invention, an interactive label as labels employing FRET (fluorescence resonance energy transfer) phenomenon permits to conveniently detect the target nucleic acid sequence in real-time manner.

Furthermore, the repetition of two successive steps, i.e., hybridization of the primer with the target nucleic acid sequence and incubation with the template-dependent nucleic acid polymerase having the 5' to 3' nuclease activity, allows for signal amplification for the target nucleic acid sequence. Therefore, the signal amplification contributes significantly to elevation of the sensitivity of target detection.

Where the THD primer is used together with a counterpart primer capable of target amplification in the present invention, signal amplification as well as target sequence amplification is simultaneously accomplished, successfully providing a homogeneous assay method.

The homogeneous assay method of the present invention is distinctly different from conventional methods developed up to now.

As methods using labeled primers for target detection, the Sunrise method (Nazarenko et al., 2516-2521 Nucleic Acids Research, 1997, v.25 no.12, and U.S. Pat. No. 6,117,635) and the Scorpion method (Whitcombe et al., 804-807, Nature Biotechnology v.17 AUGUST 1999 and U.S. Pat. No. 6,326,145) were proposed. These methods generate target indicative signals by only primer extension and employ no 5' to 3' nuclease activity of nucleic acid polymerases; however, this nuclease activity is responsible for signal generation in the present method. Such difference in signal generation mechanism permits the present invention to more easily detect a target nucleic acid sequence even by no use of primers with a complex structure necessary for the existing methods.

U.S. Pat. No. 6,248,526 discloses a target detection method using labeled primers and nucleic acid polymerases. This method employs the 3' to 5' proofreading activity of nucleic acid polymerases to cleave a 3'-end portion of labeled primers for signal generation. In short, the conventional method uses a nuclease activity different from the present method. In the case using the 3' to 5' proofreading nuclease activity of nucleic acid polymerases, it is troublesome to design target-hybridizable primers carrying mismatch at the 3'-end. Where the primer is hybridized with a non-target sequence except for its mismatch sequence at the 3'-end, the mismatch sequence is cleaved by the 3' to 5' proofreading nuclease activity to generate false positive signals. However, the present invention needs no a mismatch sequence and therefore is free from the problems of the conventional method.

The TaqMan probe method using the 5' to 3' nuclease activity of nucleic acid polymerases is predominantly used in the art for target detection (U.S. Pat. No. 5,210,015). The method requires labeled probes and upstream primers for target indicative signal generation.

The TaqMan probe technology suggests two approaches for signal generation: polymerization-dependent cleavage and polymerization-independent cleavage. In polymerization-dependent cleavage, extension of the upstream primer must occur before a nucleic acid polymerase encounters the 5'-end of the labeled probe. As the extension reaction continues, the polymerase progressively cleaves the 5'-end of the labeled probe. In polymerization-independent cleavage, the upstream primer and the labeled probe are hybridized with a target nucleic acid in close proximity such that binding of the nucleic acid polymerase to the 3'-end of the upstream primer puts it in contact with the 5'-end of the labeled probe to release the label. As described above, the TaqMan probe technology demands not only labeled probes but also upstream primers for signal generation. The labeled probes are not involved in target amplification.

Unlike the TaqMan probe technology, the present invention utilizes the 5' to 3' nuclease activity of nucleic acid polymerases in an independent fashion for signal generation in which the 5' to 3' nuclease activity exhibits its nucleolytic activity with no help of other activities (e.g., polymerization activity) and other additives (e.g., upstream primers). The present invention links labels to primers not probes as the TaqMan probe technology.

The present inventors have made intensive researches to overcome shortcomings associated with conventional technologies for detection of target nucleic acid sequences. The present inventors have devised new analytic-functional primers with a dual surveillance function, i.e., probing and priming, and have in turn constructed various protocols using the oligonucleotides for detection of target nucleic acid sequences. As results, we have verified that the new protocols or processes exhibit a plausible performance in detection of target nucleic acid sequences, inter alia, real-time detection, and produce signals indicating a target nucleic acid sequence in much stronger and faster manner.

The key discovery of the present inventors is that when a primer hybridized with a target nucleic acid sequence is contacted to a template-dependent nucleic acid polymerase having a 5' to 3' nuclease activity under conditions for the 5'-cleavage reaction and the 3'-extension reaction of the primer by the template-dependent nucleic acid polymerase, its 3'-end is extended and its 5'-end portion is also cleaved, which is the basis governing the present invention. Based on these findings and discoveries, when a label generating a detectable signal has been incorporated into a primer to generate amplicons in PCR reactions, a signal has been found to generate during real-time PCR reactions. This application has turned out to be more efficient in target detection than existing methods where additional probes or modification of primers are required. The labeled primer of the present invention can not only provide incomparably powerful and flexible tool for effective detection of target nucleic acid sequences, but also make the development process of real-time PCR assays simpler, shorter and more economical.

In one aspect of the present invention, there is provided a method for detecting a target nucleic acid sequence from a DNA or a mixture of nucleic acids using a 5'-cleavage reaction and a 3'-extension reaction of a target hybridization and detection primer (THD primer), which comprises the steps of:

(a) hybridizing the target nucleic acid sequence with the THD primer; wherein the THD primer comprises (i) a hybridizing nucleotide sequence complementary to the target nucleic acid sequence and (ii) a label or an interactive label system containing a plurality of labels;

(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained; and (c) detecting the signal indicative of the presence of the target nucleic acid sequence.

According to the present invention, the oligonucleotide to be hybridized with a target nucleic acid sequence shows a dual function upon hybridization with a target nucleic acid sequence: a first function, synthesis of complementary sequence; a second function, generation of signals indicating a target nucleic acid sequence.

Therefore, the oligonucleotide is called a "Target Hybridization and Detection primer" (THD primer) and the present method called "THD primer Target Detection Assay".

According to the present invention, a target nucleic acid sequence is first hybridized with the THD primer.

The term used herein "target nucleic acid", "target nucleic acid sequence" or "target sequence" refers to a nucleic acid sequence of interest for detection, which is annealed to or hybridized with a primer or probe under hybridization, annealing or amplifying conditions.

The term "primer" as used herein refers to an oligonucleotide, which is capable of acting as a point of initiation of synthesis when placed under conditions in which synthesis of primer extension product which is complementary to a nucleic acid strand (template) is induced, i.e., in the presence of nucleotides and an agent for polymerization, such as DNA polymerase, and at a suitable temperature and pH. The primer is preferably single stranded for maximum efficiency in amplification. Preferably, the primer is an oligodeoxyribonucleotide. The primer of this invention may be comprised of naturally occurring dNMP (i.e., dAMP, dGM, dCMP and dTMP), modified nucleotide, or non-natural nucleotide. The primer may also include ribonucleotides.

The primer must be sufficiently long to prime the synthesis of extension products in the presence of the agent for polymerization. The exact length of the primers will depend on many factors, including temperature, application, and source of primer. The term "annealing" or "priming" as used herein refers to the apposition of an oligodeoxynucleotide or nucleic acid to a template nucleic acid, whereby the apposition enables the polymerase to polymerize nucleotides into a nucleic acid molecule which is complementary to the template nucleic acid or a portion thereof.

The term used "hybridizing" used herein refers to the formation of a double-stranded nucleic acid from complementary single stranded nucleic acids. There is no intended distinction between the terms "annealing" and "hybridizing", and these terms will be used interchangeably.

The term "THD primer" used herein means a primer in that upon hybridization with the target nucleic acid sequence, it induces the production of a complementary sequence of the target nucleic acid and its 5'-end portion is cleaved by a template-dependent nucleic acid polymerase having a 5' to 3' nuclease activity.

The term used herein "forward primer" means a primer complementary to a strand of a nucleic acid sequence aligned in a 3' to 5' direction. The reverse primer has a complementary sequence to the other strand of the nucleic acid sequence.

The term used herein "upstream primer" refers to a primer to be hybridized with a site upstream of a hybridized site of a primer of interest and has the same orientation as the primer of interest.

The term used herein "downstream primer" refers to a primer to be hybridized with a site downstream of a hybridized site of a primer of interest and has the same orientation as the primer of interest.

The THD primer comprises (i) a hybridizing nucleotide sequence complementary to the target nucleic acid sequence and (ii) a label or an interactive label system containing a plurality of labels. The term "complementary" is used herein to mean that primers or probes are sufficiently complementary to hybridize selectively to a target nucleic acid sequence under the designated annealing conditions or stringent conditions, encompassing the terms "substantially complementary" and "perfectly complementary", preferably perfectly complementary.

According to a preferred embodiment, the 5'-end or a 5'-end portion of the THD primer has a perfectly complementary to the target nucleic acid sequence.

The term used herein "5'-end portion" in conjunction with the THD primer refers to a portion or region comprising any lengthy consecutive sequence from the 5'-end of the THD primer. Preferably, the 5'-end portion of the THD primer is composed of a sequence comprising 1-10 nucleotides (more preferably 1-5 nucleotides, still more preferably 1-3 nucleotides) from its 5'-end.

The label generating a detectable signal useful in the present invention includes any label known to one of skill in the art. Most of labels are composed of a single molecule or a single atom label; however some labels (e.g., interactive label system) composed of at least two or more label molecules or atoms.

According to a preferred embodiment, the THD primer comprises at least one label on its 5'-end portion (more preferably, any site of a sequence comprising 1-10 nucleotides from its 5'-end, still more preferably, any site of a sequence comprising 1-5 nucleotides from its 5'-end, still much more preferably, any site of a sequence comprising 1-3 nucleotides from its 5'-end). Most preferably, the THD primer comprises at least one label at its 5'-end.

Where the 5' to 3' nuclease activity of template-dependent nucleic acid polymerases is a 5' to 3' exonuclease activity, the label linked to the 5'-end of the THD primer may be cleaved by the exonuclease activity. Where the 5' to 3' nuclease activity of template-dependent nucleic acid polymerases is a 5' to 3' endonuclease activity, the label linked to a site 1-3 nucleotides apart from the 5'-end of the THD primer may be cleaved by the endonuclease activity.

One or more labels (preferably one label) may be linked its 5'-end portion of the THD primer, except for the interactive label system containing at least two label molecules. For example, in the case of using the interactive label system composed of a pair of a donor molecule and an acceptor molecule is used, one member of the pair may be linked to the 5'-end portion of the THD primer and the other member linked to any site of the THD primer so long as energy transfer between two molecules occurs.

According to a preferred embodiment, the label generating the detectable signal is a chemical label, an enzymatic label, a radioactive label, a fluorescent label, a luminescent label, a chemiluminescent label or a metal label (e.g., gold).

The chemical label includes biotin. The binding specificity of biotin to streptavidin (or avidin) allows for an indirect signal generation indicative of target nucleic acid sequences.

The enzymatic label includes alkaline phosphatase, β-galactosidase, β-glucosidase, luciferase, cytochrome $P_{450}$ and horseradish peroxidase. Using substrates for the enzymatic labels, the signal indicative of target nucleic acid sequences may be obtained. Where using alkaline phosphatase, bromo-chloroindolylphosphate (BCIP), nitro blue tetrazolium (NBT) or ECF may be used as a substrate for color-developing reactions in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) or naphtol/pyronine may be used as a substrate; and in the case of using glucose oxidase, t-NBT (nitroblue tetrazolium) or m-PMS (phenzaine methosulfate) may be used as a substrate.

The radioactive label includes $C^{14}$, $I^{125}$, $P^{32}$ and $S^{35}$.

According to a preferred embodiment of the present invention, the label linked to THD primer is a single label capable of providing real-time signal. For example, the single label is fluorescent terbium chelat (Nurmi et al, *Nucleic Acids Research*, 2000, Vol. 28 No. 8). Nurmi et al disclose that the label emits low level of fluorescence in a probe-linked form, but when the label is released from the probe-template duplex by 5' to 3' nucleolytic activity, the fluorescence signal is enhanced. Therefore, the fluorescent terbium chelate allows real-time target detection even though a single label is linked to a probe or THD primer for the prevent invention.

The interactive label system is a signal generating system in which energy is passed non-radioactively between a donor molecule and an acceptor molecule.

As a representative of the interactive label system, the FRET (fluorescence resonance energy transfer) label system includes a fluorescent reporter molecule (donor molecule) and a quencher molecule (acceptor molecule). In FRET, the energy donor is fluorescent, but the energy acceptor may be fluorescent or non-fluorescent.

In another form of interactive label systems, the energy donor is non-fluorescent, e.g., a chromophore, and the energy acceptor is fluorescent. In yet another form of interactive label systems, the energy donor is luminescent, e.g. bioluminescent, chemiluminescent, electrochemiluminescent, and the acceptor is fluorescent.

More preferably, the signal indicative of the target nucleic acid sequence is generated by interactive label systems, most preferably the FRET label system.

Where the FRET label is used, the two labels (the fluorescent reporter molecule and a quencher molecule positioned on the THD primer to quench the fluorescence of the reporter molecule) are separated by a site within the THD primer susceptible to nuclease cleavage, whereby allowing the 5' to 3' nuclease activity of the template-dependent nucleic acid polymerase to separate the fluorescent reporter molecule from the quencher molecule by cleaving at the susceptible site thereby obtaining the signal indicative of the presence of the target nucleic acid sequence.

According to a preferred embodiment, the fluorescent reporter molecule is located on a 5'-end portion (more preferably, at the 5'-end) of the THD primer and the quencher molecule is located downstream from the fluorescent reporter molecule. Alternatively, the quencher molecule is located on a 5'-end portion (more preferably, at the 5'-end) of the THD primer and the fluorescent reporter molecule is located downstream from the quencher molecule.

The reporter molecule and the quencher molecule useful in the present invention may be fluorescent materials. Reporter molecules and quencher molecules known in the art are useful in this invention. Examples of those are: Cy2™ (506), YO-PRO™-1 (509), YOYO™-1 (509), Calcein (517), FITC (518), Fluor X™ (519), Alexa™ (520), Rhodamine 110 (520), 5-FAM (522), Oregon Green™ 500 (522), Oregon Green™ 488 (524), RiboGreen™ (525), Rhodamine Green™ (527), Rhodamine 123 (529), Magnesium Green™ (531), Calcium Green™ (533), TO-PRO™-1 (533), TOTO1 (533), JOE (548), BODIPY530/550 (550), DiI (565), BODIPY TMR (568), BODIPY558/568 (568), BODIPY564/570 (570), Cy3™ (570), Alexa™ 546 (570), TRITC (572), Magnesium Orange™ (575), Phycoerythrin R&B (575), Rhodamine Phalloidin (575), Calcium Orange™ (576), Pyronin Y (580), Rhodamine B (580), TAMRA (582), Rhodamine Red™ (590), Cy3.5™ (596), ROX (608), Calcium Crimson™ (615), Alexa™ 594 (615), Texas Red (615), Nile Red (628), YO-PRO™-3 (631), YOYO™-3 (631), R-phycocyanin (642), C-Phycocyanin (648), TO-PRO™-3 (660), TOTO3 (660), DiD DilC(5) (665), Cy5™ (670), Thiadicarbocyanine (671) and Cy5.5 (694). The numeric in parenthesis is a maximum emission wavelength in nanometer.

Suitable pairs of reporter-quencher are disclosed in a variety of publications as follows: Pesce et al., editors, Fluorescence Spectroscopy (Marcel Dekker, New York, 1971); White et al., Fluorescence Analysis: A Practical Approach (Marcel Dekker, New York, 1970); Berlman, Handbook of Fluorescence Spectra of Aromatic Molecules, $2^{nd}$ Edition (Academic Press, New York, 1971); Griffiths, Color AND Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); Haugland, R. P., Handbook of Fluorescent Probes and Research Chemicals, $6^{th}$ Edition, Molecular Probes, Eugene, Oreg., 1996; U.S. Pat. Nos. 3,996,345 and 4,351,760.

It is noteworthy that a non-fluorescent black quencher molecule capable of quenching a fluorescence of a wide range of wavelengths or a specific wavelength may be used in the present invention.

In the FRET label adapted to the THD primer, the reporter encompasses a donor of FRET and the quencher encompasses the other partner (acceptor) of FRET. For example, a fluorescein dye is used as the reporter and a rhodamine dye as the quencher.

The present invention employs two separate activities of the template-dependent nucleic acid polymerase including a polymerase activity and a 5' to 3' nuclease activity. The term "5' to 3' nuclease activity" used herein means either 5' to 3' exonuclease activity generally associated with DNA polymerases whereby nucleotides are removed from the 5'-end of an oligonucleotide hybridized to a template, or 5' to 3' endonuclease activity wherein cleavage occurs more than one nucleotide from the 5'-end of an oligonucleotide hybridized to a template.

The reaction catalyzed by the polymerase activity is expressed herein as 3'-extension reaction. The reaction catalyzed by the 5' to 3' nuclease activity is expressed herein as 5'-cleavage reaction.

The 5'-cleavage reaction refers to a nucleolytic reaction at the 5'-end or on a 5'-end potion (e.g., more than one nucleotide apart from the 5'-end) of an oligonucleotide (e.g., primers and probes) hybridized with the target nucleic acid sequence. This reaction results in cleavage of primers and probes, giving nucleotide fragments with various sizes.

The 3'-extension reaction refers to a polymerization reaction of nucleic acids at the 3'-end of primers by a template-dependent nucleic acid polymerase.

The expression used herein "release of labels" encompasses release of labels per se or release of nucleotide fragment(s) containing label(s). Where the oligonucleotide (e.g., primers and probes) used in the present invention contains at least two labels, the expression "releases of labels" means release of at least one label or release of at least one nucleotide fragment containing at least one label.

The expression used herein "release of at least one label of the interactive label system" refers to release of at least one label per se among a plurality of labels constituting the interactive label system, or release of nucleotide fragment(s) containing at least one label.

The present invention generally includes six illustrative protocols for detecting target nucleic acid sequences, but not limited to:

The first protocol is to detect target nucleic acid sequences using only THD primer.

The second protocol is to detect target nucleic acid sequences using the THD primer together with a labeled probe.

The third protocol is to detect target nucleic acid sequences using the THD primer together with an upstream primer (or a downstream primer).

The fourth protocol is to detect target nucleic acid sequences using a primer pair composed of two primers as a forward primer and a reverse primer in which at least one primer is the THD primer.

The fifth protocol is to detect target nucleic acid sequences using (i) a primer pair composed of two primers as a forward primer and a reverse primer in which at least one primer is the THD primer, and (ii) a labeled probe.

The sixth protocol is to detect target nucleic acid sequences using (i) a primer pair composed of two primers as a forward primer and a reverse primer in which at least one primer is the THD primer, and (ii) an upstream primer (or a downstream to primer).

All the detection protocols will be described in more detail as follows:

1. THD Primer Target Detection Assay Using THD Primer

In accordance with the first protocol as the most basic process of this invention, when the THD primer hybridized with the target nucleic acid sequence is extended, it is cleaved by the template-dependent nucleic acid polymerase having the 5' to 3' nuclease activity to release the label from the THD primer, whereby a signal indicative of the presence of the target nucleic acid sequence is obtained.

The first protocol comprises the steps of:

(a) hybridizing the target nucleic acid sequence with the THD primer; wherein the THD primer comprises (i) a hybridizing nucleotide sequence complementary to the target nucleic acid sequence and (ii) a label or an interactive label system containing a plurality of labels;

(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained; and (c) detecting the signal indicative of the presence of the target nucleic acid sequence.

FIG. 1 shows the basic schematic steps of the first protocol and FIG. 5 shows the result of the detection of a target nucleic acid sequence using the THD primer of this invention and Taq DNA polymerase without the repetition of denaturation, hybridization, cleavage and extension at a predetermined time interval.

Preferably, the method further comprises the step of repeating the steps (a)-(b) or (a)-(c) with denaturation between repeating cycles at least twice to amplify the signal indicative of the presence of the target nucleic acid sequence. The cycle repetition allows for cleavage of the THD primer hybridized with the target nucleic acid sequence, contributing to amplification of the signal indicative of the presence of the target nucleic acid sequence. Such a signal amplification is deemed as a real-time signal amplification.

Preferably, the first protocol comprises the steps of:

(a) hybridizing the target nucleic acid sequence with the THD primer; wherein the THD primer comprises (i) a hybridizing nucleotide sequence complementary to the target nucleic acid sequence and (ii) a label or an interactive label system containing a plurality of labels;

(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained;

(b') denaturing the resultant of step (b);

(b") repeating the steps (a)-(b') at least twice to amplify the signal indicative of the presence of the target nucleic acid sequence; and (c) detecting the signal indicative of the presence of the target nucleic acid sequence, wherein the detection is performed for each cycle of the repetition of step (b"), at the end of the repetition of step (b") or at each of a predetermined time intervals during the repetition of step (b"), such that the signal is indicative of the presence of the target nucleic acid sequence.

Figure 6:
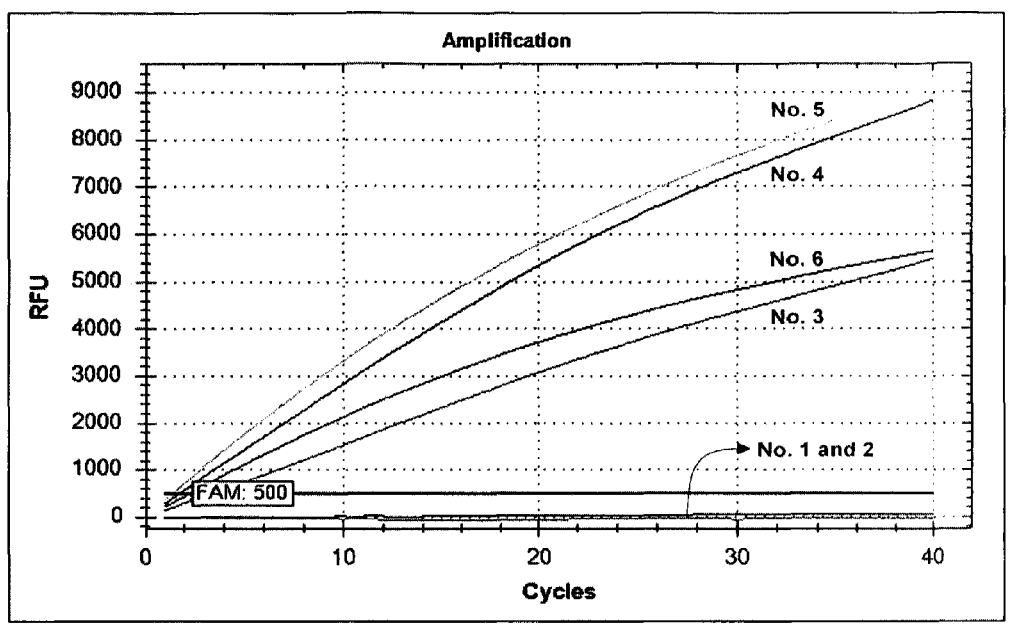
FIG. 6 shows the results of the real-time signal amplification using a THD primer and Taq DNA polymerase with the repetition of denaturation, hybridization, cleavage and extension at the various concentrations of dNTPs.

This method comprising the repeating step is schematically illustrated in FIG. 2 and FIG. 6 shows the results of the real-time signal amplification using the THD primer and Taq DNA polymerase with the repetition of denaturation, hybridization, cleavage and extension at the various concentrations of dNTPs.

According the first protocol, the signal indicative of the presence of the target nucleic acid sequence is obtained or amplified by only cleavage reaction at the THD primer.

The denaturation of the resultant of step (b) is to render the double stranded duplexes formed in step (b) into single stranded nucleic acids. Methods for denaturation includes, but not limited to, heating, alkali, formamide, urea and glycoxal treatment, enzymatic methods (e.g., helicase action) and binding proteins. For instance, the denaturation may be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y.(2001).

According to a preferred embodiment, the detection of the signal is performed in a real-time manner, an end-point manner or a predetermined time interval manner. The detection in the real-time manner is to detect the signal for each cycle of the repetition. The detection in the end-point manner is to detect the signal at the end of the repetition. The detection in the predetermined time interval manner is to detect the signal at each of a predetermined time intervals during the repetition.

The present invention is very suited for multiplex detection of target nucleic acid sequences.

According to a preferred embodiment, the target nucleic acid sequence comprises at least two types (more preferably at least three types, most preferably at least five types) of nucleic acid sequences and the THD primer comprises at least two types (more preferably at least three types, most preferably at least five types) of primers.

Where at least two THD primers are used, they may be prepared to contain labels in various combinations depending on analysis purposes. For instance, a plurality of the THD primers may be linked with all the identical labels, all different labels or partial different labels. In addition, at least two partially or wholly different or same labels may be linked to one THD primer.

According to a preferred embodiment, the target nucleic acid sequence comprises a nucleotide variation.

According to a preferred embodiment, the target nucleic acid sequence is a pre-amplified nucleic acid sequence. The utilization of the pre-amplified nucleic acid sequence in the present invention allows for a striking increase in sensitivity and specificity for target detection. A minute amount of the target nucleic acid sequence is pre-amplified to a suitable level and then detected by the present invention, permitting the sensitivity of the target detection to be highly increased. Interestingly, the THD primer hybridizable with sequences downstream of primers used in the pre-amplification reaction may serve as nested primers for increasing the specificity of the target detection.

2. THD Primer Target Detection Assay Using THD Primer and Labeled Probe

The second protocol uses a labeled probe as well as the THD primer. The labeled probe has a label generating a detectable signal and the labeled probe is hybridized with a site downstream of a hybridized site of the THD primer and has the same orientation as the THD primer, and is cleaved in successive steps.

The 3'-end of the labeled probe is blocked to prohibit extension of the probe. Blocking can be achieved by using non-complementary bases or by adding a chemical moiety such as biotin or a phosphate group to the 3' hydroxyl of the last nucleotide. Blocking can also be achieved by removing the 3'-OH or by using a nucleotide that lacks a 3'-OH such as a dideoxynucleotide.

The term used herein "probe" refers to a single-stranded nucleic acid molecule comprising a portion or portions that are substantially complementary to a target nucleic acid sequence.

The second protocol may produce higher signal intensity for target nucleic acid sequences compared with the first protocol using only the THD primer, because the signal is generated from the labeled probe as well as the THD primer.

The label useful in the labeled probe is described as that in the THD primer. Preferably, the label is a FRET label.

The labeled probe is also cleaved by the template-dependent nucleic acid polymerase having the 5' to 3' nuclease activity to release the label from the labeled probe. Therefore, the second protocol gives two separate signals indicative of the presence of the target nucleic acid sequence.

According the second protocol, when the THD primer hybridized with the target nucleic acid sequence is extended, the 5'-cleavage reaction occurs on the THD primer, and/or the labeled probe by the template-dependent nucleic acid polymerase having the 5' to 3' nuclease activity to release the label from the THD primer and/or the labeled probe, whereby a signal indicative of the presence of the target nucleic acid sequence is obtained.

The second protocol comprises the steps of:
(a) hybridizing the target nucleic acid sequence with the THD primer and a labeled probe; wherein the THD primer comprises (i) a hybridizing nucleotide sequence complementary to the target nucleic acid sequence and (ii) a label or an interactive label system containing a plurality of labels;
(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer; wherein the labeled probe is cleaved by the 5' to 3' nuclease activity of the template-dependent nucleic acid polymerase to release the label from the probe, whereby a signal indicative of the presence of the target nucleic acid sequence is obtained; and
(c) detecting the signal indicative of the presence of the target nucleic acid sequence.

Preferably, the second protocol further comprises the step of repeating the steps (a)-(b) or (a)-(c) with denaturation between repeating cycles at least twice to amplify the signal indicative of the presence of the target nucleic acid sequence.

Specifically, the second protocol comprises the steps of:
(a) hybridizing the target nucleic acid sequence with the THD primer and a labeled probe; wherein the THD primer comprises (i) a hybridizing nucleotide sequence complementary to the target nucleic acid sequence and (ii) a label or an interactive label system containing a plurality of labels; wherein the labeled probe is hybridized with a site downstream of a hybridized site of the THD primer and has the same orientation as the THD primer;
(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer; wherein the labeled probe is cleaved by the 5' to 3' nuclease activity of the template-dependent nucleic acid polymerase to release the label from the probe, whereby a signal indicative of the presence of the target nucleic acid sequence is obtained;
(b') denaturing the resultant of step (b);
(b") repeating the steps (a)-(b') at least twice to amplify the signal indicative of the presence of the target nucleic acid sequence; and
(c) detecting the signal indicative of the presence of the target nucleic acid sequence, wherein the detection is performed for each cycle of the repetition of step (b"), at the end of the repetition of step (b") or at each of a predetermined time intervals during the repetition of step (b"), such that the signal is indicative of the presence of the target nucleic acid sequence.

According to a preferred embodiment, the target nucleic acid sequence comprises at least two types (more preferably at least three types, most preferably at least five types) of nucleic acid sequences, the THD primer comprises at least two types (more preferably at least three types, most preferably at least five types) of primers and the labeled probe comprises at least two types (more preferably at least three types, most preferably at least five types) of probes.

Where at least two THD primers and at least two probes are used, they may be prepared to contain labels in various combinations depending on analysis purposes. For instance, a plurality of the THD primers and at least two probes may be linked with all the identical labels, all different labels or partial different labels. In addition, at least two partially or wholly different or same labels may be linked to one THD primer or one probe.

According to a preferred embodiment, the target nucleic acid sequence comprises a nucleotide variation.

According to a preferred embodiment, the target nucleic acid sequence is a pre-amplified nucleic acid sequence.

3. THD Primer Target Detection Assay Using THD Primer and Upstream (or Downstream Primer)

According the third protocol, when the THD primer and an upstream primer (or downstream primer) hybridized with the target nucleic acid sequence are extended, the 5'-cleavage reaction occurs on the THD primer and/or the upstream primer (or downstream primer) by the template-dependent nucleic acid polymerase having the 5' to 3' nuclease activity to release the label from the THD primer, whereby a signal indicative of the presence of the target nucleic acid sequence is obtained.

The upstream primer is hybridized with a site upstream of a hybridized site of the THD primer and has the same orientation as the THD primer. The downstream primer is hybridized with a site downstream of a hybridized site of the THD primer and has the same orientation as the THD primer.

Specifically, the third protocol comprises the steps of:

(a) hybridizing the target nucleic acid sequence with the THD primer and an upstream primer or downstream primer; wherein the THD primer comprises (i) a hybridizing nucleotide sequence complementary to the target nucleic acid sequence and (ii) a label or an interactive label system containing a plurality of labels; wherein the upstream primer is hybridized with a site upstream of a hybridized site of the THD primer and has the same orientation as the THD primer; wherein the downstream primer is hybridized with a site downstream of a hybridized site of the THD primer and has the same orientation as the THD primer;

(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained;

(c) detecting the signal indicative of the presence of the target nucleic acid sequence.

Preferably, the method further comprises the step of repeating the steps (a)-(b) or (a)-(c) with denaturation between repeating cycles at least twice to amplify the signal indicative of the presence of the target nucleic acid sequence. The cycle repetition allows for cleavage of the THD primer hybridized with the target nucleic acid sequence, contributing to amplification of the signal indicative of the presence of the target nucleic acid sequence.

Specifically, the third protocol comprises the steps of:

(a) hybridizing the target nucleic acid sequence with the THD primer and an upstream primer or downstream primer; wherein the THD primer comprises (i) a hybridizing nucleotide sequence complementary to the target nucleic acid sequence and (ii) a label or an interactive label system containing a plurality of labels; wherein the upstream primer is hybridized with a site upstream of a hybridized site of the THD primer and has the same orientation as the THD primer; wherein the downstream primer is hybridized with a site downstream of a hybridized site of the THD primer and has the same orientation as the THD primer;

(b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained;

(b') denaturing the resultant of step (b);

(b") repeating the steps (a)-(b') at least twice to amplify the signal indicative of the presence of the target nucleic acid sequence; and (c) detecting the signal indicative of the presence of the target nucleic acid sequence, wherein the detection is performed for each cycle of the repetition of step (b"), at the end of the repetition of step (b") or at each of a predetermined time intervals during the repetition of step (b"), such that the signal is indicative of the presence of the target nucleic acid sequence.

According to a preferred embodiment, the upstream primer or the downstream primer has a label generating a detectable signal. The label linked to the upstream primer or the downstream primer may be released in step (b) along with that linked to the THD primer and be also involved in the signal in step (c). In an embodiment, the label linked to the upstream primer or the downstream primer is different from that linked to the THD primer. The label useful in the upstream primer or the downstream primer is described as that in the THD primer. Preferably, the label is a FRET label.

Where the upstream primer or the downstream primer has a label, the third protocol may produce higher signal intensity for target nucleic acid sequences compared with the first protocol using only the THD primer because the signal is generated from the labeled upstream primer (or the labeled downstream primer) as well as the THD primer.

According to a preferred embodiment, the target nucleic acid sequence comprises at least two types (more preferably at least three types, most preferably at least five types) of nucleic acid sequences, the THD primer comprises at least two types (more preferably at least three types, most preferably at least five types) of primers and the upstream primer (or downstream primer) comprises at least two types (more preferably at least three types, most preferably at least five types) of primers.

According to a preferred embodiment, the target nucleic acid sequence comprises a nucleotide variation.

According to a preferred embodiment, the target nucleic acid sequence is a pre-amplified nucleic acid sequence.

4. Real-Time Target Amplification Assay Using THD Primer

In accordance with the fourth protocol, when the primer pair composed of two primers as a forward primer and a reverse primer in which at least one primer is the THD primer, that is hybridized with the target nucleic acid sequence, are extended, the 5'-cleavage reaction occurs on the two primers by the template-dependent nucleic acid polymerase having the 5' to 3' nuclease activity to release the label from the THD primer, whereby a signal indicative of the presence of the target nucleic acid sequence is obtained (FIG. 3).

A primer pair composed of two primers as a forward primer and a reverse primer in which at least one primer is the THD primer enables both target amplification and signal amplification when the procedure is repeatedly carried out.

According to a preferred embodiment, the present method comprises the steps of:

(a) hybridizing the target nucleic acid sequence with a primer pair composed of two primers as a forward primer and a reverse primer in which at least one primer is the THD primer capable of amplifying the target nucleic acid sequence; wherein the THD primer comprises (i) a hybridizing nucleotide sequence complementary to the target nucleic acid sequence and (ii) a label or an interactive label system containing a plurality of labels;

(b) contacting the resultant of step (a) to a template-dependent nucleic acid polymerase having a 5' to 3' nuclease activity under conditions for the 5'-cleavage reaction and the 3'-extension reaction of the two primers by the template-dependent nucleic acid polymerase, wherein the two primers are extended by the polymerase activity of the template-dependent nucleic acid polymerase and cleaved by the 5' to 3' nuclease activity of the template-dependent nucleic acid polymerase to release the label, or at least one label of the interactive label system from the THD primer among the two primers, whereby a signal indicative of the presence of the target nucleic acid sequence is obtained;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of predetermined time intervals during the repetition, such that the signal is indicative of the presence of the target nucleic acid sequence.

The fourth protocol utilizes a primer pair composed of two primers as a forward primer and a reverse primer. At least one of the two primers is the THD primer.

According to a preferred embodiment, the step (a) is performed using at least one additional primer having a reverse orientation to the THD primer. At this case, the templates (i.e. the target nucleic sequence) are more available for the hybridization of the THD primer.

According to a preferred embodiment, the two primers all has a label to be released in step (b). The labels linked to the two primers may be the same or different from each other. The label useful in the counterpart primer of the THD primer is described as that in the THD primer. Preferably, the label is a FRET label.

The denaturation of the resultant of step (b) is to render the double stranded duplexes formed in step (b) into single stranded nucleic acids. Methods for denaturation includes, but not limited to, heating, alkali, formamide, urea and glycoxal treatment, enzymatic methods (e.g., helicase action) and binding proteins. For instance, the denaturation may be achieved by heating at temperature ranging from 80° C. to 105° C. General methods for accomplishing this treatment are provided by Joseph Sambrook, et al., *Molecular Cloning, A Laboratory Manual*, Cold Spring Harbor Laboratory Press, Cold Spring Harbor, N.Y.(2001).

The present invention is very suited for multiplex detection of target nucleic acid sequences. To our best knowledge, the present invention is a sole method to permits a multiplex real-time detection to come true.

In the fourth protocol, various combinations of the THD primer can be prepared as shown in FIG. 4A: (A) the THD primer as a forward primer; (B) the THD primer as a reverse primer; and (C) the THD primer as a forward primer and a reverse primer.

Figure 15:
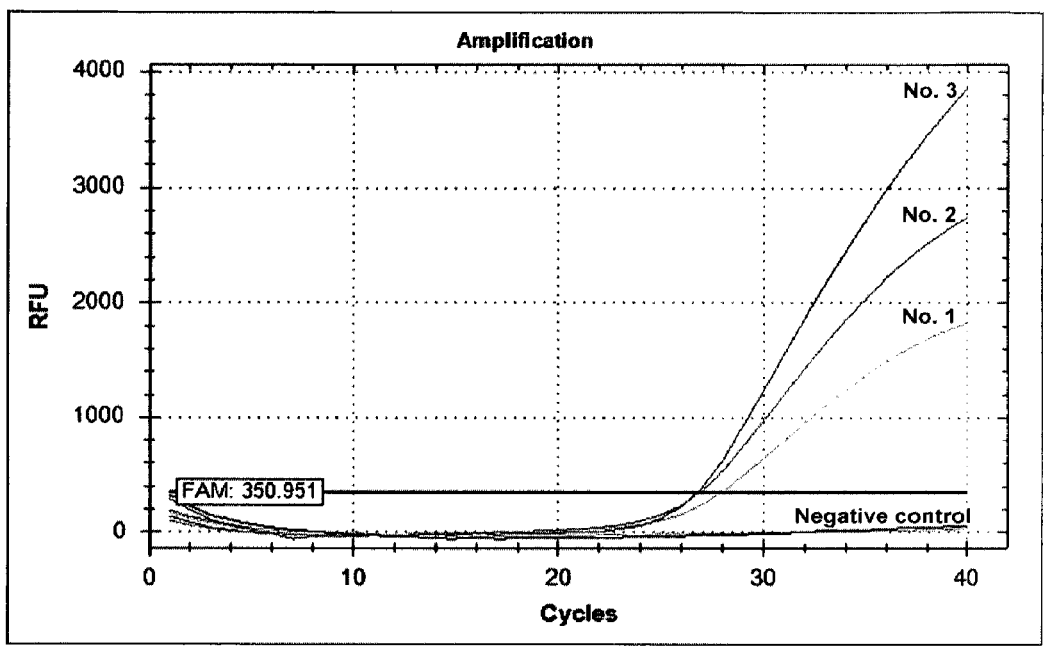
FIG. 15 shows the results used a THD primer as a forward primer, a reverse primer or both in the real-time PCR amplification for *Neisseria gonorrhoeae* (NG) gene.

FIG. 15 shows the results of primer combinations illustrated in FIG. 4A using the THD primer as a forward primer, a reverse primer or both in the real-time PCR amplification for *Neisseria gonorrhoeae* (NG) gene According to a preferred embodiment, the target nucleic acid sequence comprises at least two types (more preferably at least three types, most preferably at least five types) of nucleic acid sequences, each of the two primers comprises at least two types (more preferably at least three types, most preferably at least five types) of primers.

According to a preferred embodiment, the target nucleic acid sequence comprises a nucleotide variation.

According to a preferred embodiment, the target nucleic acid sequence is a pre-amplified nucleic acid sequence. Where the present method is performed using the pre-amplified nucleic acid sequence as a starting material, a nested amplification is induced to significantly improve the sensitivity and specificity in the target detection.

5. Real-time Target Amplification Assay Using THD Primer and Labeled Probe

The fifth protocol uses a labeled probe as well as a primer pair composed of two primers as a forward primer and a reverse primer in which at least one primer is the THD primer. The labeled probe has a label generating a detectable signal and the labeled probe is hybridized with a site downstream of a hybridized site of the THD primer and has the same orientation as the THD primer, and is cleaved in successive steps. When the two primers are hybridized with the target nucleic acid sequence and extended, the 5'-cleavage reaction occurs on the two primers by the template-dependent nucleic acid polymerase having the 5' to 3' nuclease activity to release the label from the THD primer among the two primers and; wherein the labeled probe is modified at its 3'-end to prevent extension by the template-dependent nucleic acid polymerase and hybridized with a site between the two primers and is cleaved to release a label linked to the labeled probe, whereby a signal indicative of the presence of the target nucleic acid sequence is obtained (FIG. 4B).

According to a preferred embodiment, the present method comprises the steps of:

(a) hybridizing the target nucleic acid sequence with a primer pair composed of two primers as a forward primer and a reverse primer in which at least one primer is the THD primer capable of amplifying the target nucleic acid sequence and with an additional labeled probe; wherein the THD primer comprises (i) a hybridizing nucleotide sequence complementary to the target nucleic acid sequence and (ii) a label or an interactive label system containing a plurality of labels; wherein the labeled probe is modified at its 3'-end to prevent extension by the template-dependent nucleic acid polymerase and hybridized with a site between the two primers;

(b) contacting the resultant of step (a) to a template-dependent nucleic acid polymerase having a 5' to 3' nuclease activity under conditions for the 5'-cleavage reaction and the 3'-extension reaction of the two primers by the template-dependent nucleic acid polymerase, wherein the two primers are extended by the polymerase activity of the template-dependent nucleic acid polymerase and cleaved by the 5' to 3' nuclease activity of the template-dependent nucleic acid polymerase to release the label, or at least one label of the interactive label system from the THD primer among the two primers; wherein the labeled probe is cleaved by the 5' to 3' nuclease activity of the template-dependent nucleic acid polymerase to release the label from the probe, whereby a signal indicative of the presence of the target nucleic acid sequence is obtained;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of a predetermined time intervals during the repetition of step (d), such that the signal is indicative of the presence of the target nucleic acid sequence.

According to a preferred embodiment, the step (a) is performed using at least one additional primer having a reverse orientation to the THD primer. At this case, the templates (i.e. the target nucleic acid sequence) are more available for the hybridization of the THD primer and the upstream primer (or downstream primer).

According to a preferred embodiment, the two primers all has a label to be released in step (b). The labels linked to the two primers may be the same or different from each other. The label useful in the counterpart primer of the THD primer is described as that in the THD primer. Preferably, the label is a FRET label.

In the fifth protocol, various combinations of the primer pair and the labeled probe can be prepared as shown in FIG. 4B: (A) the THD primer as a forward primer; (B) the THD primer as a reverse primer; and (C) the THD primer as a forward primer and a reverse primer.

Figure 16:
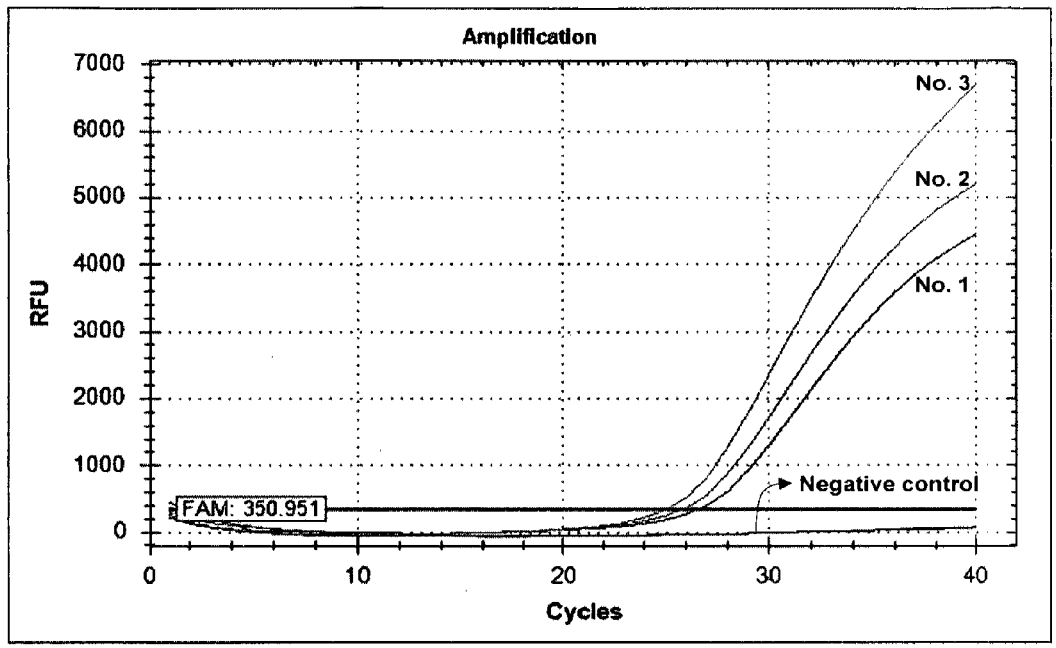
FIG. 16 shows the results used the labeled probe combined with a THD primer as a forward primer, a reverse primer or both in the real-time PCR amplification for *Neisseria gonorrhoeae* (NG) gene.

FIG. 16 shows the results of primer combinations illustrated in FIG. 4B using the labeled probe combined with the THD primer as a forward primer, a reverse primer or both in the real-time PCR amplification for *Neisseria gonorrhoeae* (NG) gene.

According to a preferred embodiment, the target nucleic acid sequence comprises at least two types (more preferably at least three types, most preferably at least five types) of nucleic acid sequences, each of the two primers as the forward primer and the reverse primer comprises at least two types (more preferably at least three types, most preferably at least five types) of primers, and the labeled probe comprises at least two types (more preferably at least three types, most preferably at least five types) of probes.

According to a preferred embodiment, the target nucleic acid sequence comprises a nucleotide variation.

According to a preferred embodiment, the target nucleic acid sequence is a pre-amplified nucleic acid sequence.

6. Real-time Target Amplification Assay Using THD primer and upstream Primer (or Downstream Primer)

According the sixth protocol, when (i) the primer pair composed of two primers as a forward primer and a reverse primer in which at least one primer is the THD primer, and (ii) the upstream primer (or the downstream primer) hybridized with the target nucleic acid sequence are extended, the 5'-cleavage reaction occurs on the two primers and/or the upstream primer (or the downstream primer) by the template-dependent nucleic acid polymerase having the 5' to 3' nuclease activity to release the label from the THD primer among the two primers, whereby a signal indicative of the presence of the target nucleic acid sequence is obtained.

According to a preferred embodiment, the present method comprises the steps of:

(a) hybridizing the target nucleic acid sequence with the primer pair composed of two primers as a forward primer and a reverse primer in which at least one primer is the THD primer, and the upstream primer (or the downstream primer); wherein the THD primer comprises (i) a hybridizing nucleotide sequence complementary to the target nucleic acid sequence and (ii) a label or an interactive label system containing a plurality of labels; wherein the upstream primer is hybridized with a site upstream of a hybridized site of the THD primer and has the same orientation as the THD primer; wherein the downstream primer is hybridized with a site between the two primers and has the same orientation as the THD primer;

(b) contacting the resultant of step (a) to a template-dependent nucleic acid polymerase having a 5' to 3' nuclease activity under conditions for the 5'-cleavage reaction and the 3'-extension reaction of the two primers and the upstream primer by the template-dependent nucleic acid polymerase, wherein the two primers and the upstream primer (or the downstream primer) are extended by the polymerase activity of the template-dependent nucleic acid polymerase and cleaved by the 5' to 3' nuclease activity of the template-dependent nucleic acid polymerase to release the label, or at least one label of the interactive label system from the THD primer among the two primers, whereby a signal indicative of the presence of the target nucleic acid sequence is obtained;

(c) denaturing the resultant of step (b);

(d) repeating the steps (a)-(c) at least twice to amplify both the target nucleic acid sequence and the signal indicative of the presence of the target nucleic acid sequence; and (e) detecting the signal indicative of the presence of the target nucleic acid sequence, wherein the detection is performed for each cycle of the repetition of step (d), at the end of the repetition of step (d) or at each of a predetermined time intervals during the repetition of step (d), such that the signal is indicative of the presence of the target nucleic acid sequence.

According to a preferred embodiment, the step (a) is performed using at least one additional primer having a reverse orientation to the THD primer. At this case, the templates (i.e. the target nucleic acid sequence) are more available for the hybridization of the THD primer and the upstream primer (or downstream primer).

According to a preferred embodiment, not only the THD primer but also other primers have a label generating a detectable signal. The labels linked to the primers may be the same or different from each other. The label useful in the primers is described as that in the THD primer. Preferably, the label is a FRET label.

In the sixth protocol, various combinations of the primer pair and an upstream primer can be constructed as shown in FIG. 4C: (A) the THD primers as a forward primer and an upstream primer; (B) the THD primers as a forward primer and a reverse primer; (C) the THD primers as a forward primer, an upstream primer and a reverse primer; and (D) the THD primer as a forward primer.

FIG. 17 shows the results of primer combinations illustrated in FIG. 4C using the THD primer as a forward primer combined with an additional THD primer as an upstream primer, a reverse primer or both in the real-time PCR amplification for *Neisseria gonorrhoeae* (NG) gene.

In the sixth protocol, various combinations of the primer pair and a downstream primer can be constructed as shown in FIG. 4D: (A) the THD primer as a Do forward primer; (B) the THD primer as a reverse primer; (C) the THD primer as a forward primer and a reverse primer.

Figure 18:
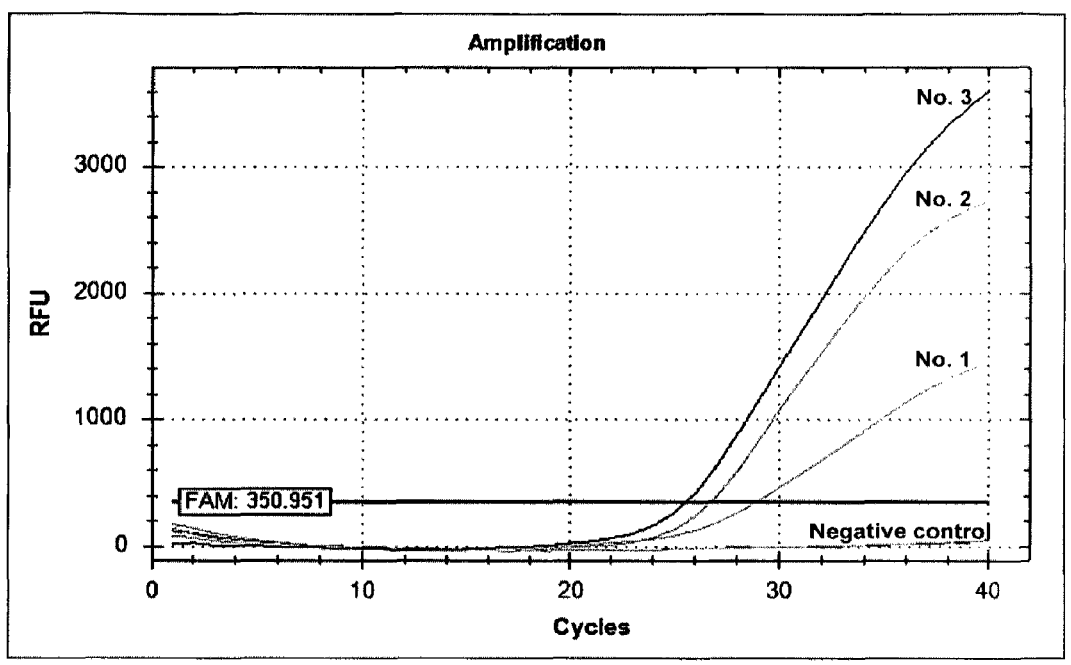
FIG. 18 shows the results used the internal primer combined with a THD primer as a forward primer, a reverse primer or both in the real-time PCR amplification for *Neisseria gonorrhoeae* (NG) gene.

FIG. 18 shows the results of primer combinations illustrated in FIG. 4D using an internal primer combined with the THD primer as a forward primer, a reverse primer or both in the real-time PCR amplification for *Neisseria gonorrhoeae* (NG) gene.

In the FIG. 4D, the downstream primer can be expressed as an internal primer.

According to a preferred embodiment, the target nucleic acid sequence comprises at least two types (more preferably at least three types, most preferably at least five types) of nucleic acid sequences, each of the two primers as the forward primer and the reverse primer comprises at least two types (more preferably at least three types, most preferably at least five types) of primers, and the upstream primer (or the downstream primer) comprises at least two types (more preferably at least three types, most preferably at least five types) of primers.

According to a preferred embodiment, the target nucleic acid sequence comprises a nucleotide variation.

According to a preferred embodiment, the target nucleic acid sequence is a pre-amplified nucleic acid sequence.

Preferable Embodiment: Real-Time PCR Assay Using THD Primer

The $4^{th}$-$6^{th}$ protocols use a primer pair composed of two primers as a forward primer and a reverse primer in which at least one primer is the THD primer capable of amplifying the target nucleic acid sequence. Therefore, the reaction repetition is accompanied with amplification of the target nucleic acid sequence. Preferably, the amplification is performed in accordance with PCR (polymerase chain reaction) which is disclosed in U.S. Pat. Nos. 4,683,195, 4,683,202, and 4,800,159.

According to a preferred embodiment, the present invention for detecting a target nucleic acid sequence from a DNA or a mixture of nucleic acids using a polymerase chain reaction (PCR) associated with a 5'-cleavage reaction and a 3'-extension reaction of a target hybridization and detection primer (THD primer), comprise the steps of:

(a) preparing a PCR mixture containing the target nucleic acid sequence, a primer pair composed of two primers in which at least one primer is the THD primer capable of amplifying the target nucleic acid sequence, and a template-dependent nucleic acid polymerase having a 5' to 3' nuclease activity; wherein the THD primer comprises (i) a hybridizing nucleotide sequence complementary to the target nucleic acid sequence and (ii) a pair of a fluorescent reporter molecule and a quencher molecule positioned on the THD primer to quench the fluorescence of the reporter molecule; wherein the two labels are separated by a site within the THD primer susceptible to nuclease cleavage, whereby allowing the 5' to 3' nuclease activity of the template-dependent nucleic acid polymerase to separate the fluorescent reporter molecule from the quencher molecule by cleaving at the susceptible site thereby obtaining the signal indicative of the presence of the target nucleic acid sequence;

(b) amplifying the target nucleic acid sequence using the PCR mixture by performing at least two cycles of primer annealing, primer extending and denaturing, wherein the two primers are extended by the polymerase activity of the template-dependent nucleic acid polymerase to amplify the target nucleic acid sequence and cleaved by the 5' to 3' nuclease activity of the template-dependent nucleic acid polymerase to release the reporter molecule or the quencher molecule from the THD primer among the two primers, whereby a signal indicative of the presence of the target nucleic acid sequence is obtained; and (c) detecting the fluorescence signal indicative of the presence of the target nucleic acid sequence, wherein the detection is performed for each cycle of the repetition of step (b), at the end of the repetition of step (c) or at each of predetermined time intervals during the repetition, such that the signal is indicative of the presence of the target nucleic acid sequence.

As described in the fourth protocol, various combinations of the THD primer in real-time PCR reactions can be suggested: (A) the THD primer as a forward primer; (B) the THD primer as a reverse primer; and (C) the THD primer as a forward primer and a reverse primer.

According to a preferred embodiment, the PCR mixture comprises a primer pair composed of two primers in which at least one primer is the THD primer, an upstream primer (or downstream primer) and the template-dependent nucleic acid polymerase having the 5' to 3' nuclease activity; wherein the upstream primer is hybridized with a site upstream of a hybridized site of the THD primer and has the same orientation as the THD primer.

According to a preferred embodiment, the PCR mixture comprises a primer pair composed of two primers in which at least one primer is the THD primer, and a labeled probe with a label generating a detectable signal; wherein the labeled probe is modified at its 3'-end to prevent extension by the template-dependent nucleic acid polymerase and hybridized with a site between the two primers.

According to a preferred embodiment, this protocol may produce higher signal intensity for target nucleic acid sequences compared to the protocol using only the primer pair, because the signal is generated from the labeled probe as well as the THD primer.

According to a preferred embodiment, the step (a) is performed using at least one additional primer having a reverse orientation to the THD primer. At this case, the templates (i.e. the target nucleic sequence) are more available for the hybridization of the THD primer.

According to a preferred embodiment, the detection of step (c) is performed in a real-time manner, an end-point manner or a predetermined time interval.

According to a preferred embodiment, the target nucleic acid sequence comprises at least two types (more preferably at least three types, most preferably at least five types) of nucleic acid sequences, each of the two primers as the forward primer and the reverse primer comprises at least two types (more preferably at least three types, most preferably at least five types) of primers.

According to a preferred embodiment, the target nucleic acid sequence comprises at least two types (more preferably at least three types, most preferably at least five types) of nucleic acid sequences, each of the two primers as the forward primer and the reverse primer comprises at least two types (more preferably at least three types, most preferably at least five types) of primers and the upstream primer (or the downstream primer) comprises at least two types (more preferably at least three types, most preferably at least five types) of primers.

According to a preferred embodiment, the target nucleic acid sequence comprises at least two types (more preferably at least three types, most preferably at least five types) of nucleic acid sequences, each of the two primers as the forward primer and the reverse primer comprises at least two types (more preferably at least three types, most preferably at least five types) of primers and the labeled probe comprises at least two types (more preferably at least three types, most preferably at least five types) of probes.

According to a preferred embodiment, not only the THD primer but also other primers have a label generating a detectable signal. The labels linked to the primers may be the same or different from each other. The label useful in the primers is described as that in the THD primer. Preferably, the label is a FRET label.

Where not only the THD primer but also other primer has a label, the higher signal intensity can be produced for target nucleic acid sequences compared with the protocol using only the THD primer because the signal is generated from other primers as well as the THD primer.

According to a preferred embodiment, the target nucleic acid sequence comprises a nucleotide variation.

According to a preferred embodiment, the target nucleic acid sequence is a pre-amplified nucleic acid sequence.

According to a preferred embodiment, the THD primer used has a dual priming oligonucleotide (DPO) structure represented by the following general formula I or a modified dual specificity oligonucleotide (mDSO) structure represented by the following general formula II:

$$5'\text{-}X_p\text{-}Y_q\text{-}Z_r\text{-}3' \quad (I)$$

wherein, $X_p$ represents a 5'-first priming portion having a hybridizing nucleotide sequence complementary to the target nucleic acid; $Y_q$ represents a separation portion comprising at least three universal bases, $Z_r$ represents a 3'-second priming portion having a hybridizing nucleotide sequence complementary to the target nucleic acid; p, q and r represent the number of nucleotides, and X, Y, and Z are deoxyribonucleotides or ribonucleotides; the $T_m$ of the 5'-first priming portion is higher than that of the 3'-second priming portion and the separation portion has the lowest $T_m$ in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the THD primer is enhanced;

$$5'\text{-}X'_p\text{-}Y'_q\text{-}Z'_r\text{-}3' \quad (II)$$

wherein, $X'_p$ represents a 5'-second priming portion having a hybridizing nucleotide sequence complementary to the target nucleic acid sequence; $Y'_q$ represents a separation portion comprising at least three universal bases, $Z'_r$ represents a 3'-first priming portion having a hybridizing nucleotide sequence complementary to the target nucleic acid sequence; p, q and r represent the number of nucleotides; and X', Y' and Z' are deoxyribonucleotides or ribonucleotides; the $T_m$ of the 5'-second priming portion is lower than that of the 3'-first priming portion and the separation portion has the lowest $T_m$ in the three portions of $X'_p$, $Y'_p$ and $Z'_r$; the separation portion separates the 5'-second priming portion from the 3'-first priming portion in terms of annealing events to the target nucleic acid sequence, the annealing specificity of the oligonucleotide are determined dually by the 5'-second priming portion and the 3'-first priming portion such that the overall annealing specificity of the THD primer is enhanced.

More preferably, the THD primer has the dual priming oligonucleotide (DPO) structure represented by the general formula I.

The THD primer having mDSO structure is particularly suitable in the third and sixth protocols using the upstream primer. The THD primer having DPO structure is suitable in other protocols.

The DPO structure as a primer version of DSO (dual specificity oligonucleotide) was first proposed by the present inventor (see WO 2006/095981; Chun et al., Dual priming oligonucleotide system for the multiplex detection of respiratory viruses and SNP genotyping of CYP2C19 gene, *Nucleic Acid Research*, 35: 6e40(2007)). The mDSO structure is a newly modified version of the DPO structure that was first proposed by the present inventor (see WO 2006/095981).

The DPO embodies a novel concept in which its hybridization or annealing is dually determined by the 5'-high $T_m$ specificity portion (or the 5'-first hybridization portion, the 5'-first priming portion) and the 3'-low $T_m$ specificity portion (or the 3'-second hybridization portion, the 3'-second priming portion) separated by the separation portion, exhibiting dramatically enhanced hybridization specificity (see WO 2006/095981; Kim et al., Direct detection of lamivudine-resistant hepatitis B virus mutants by multiplex PCR using dual-priming oligonucleotide primers, *Journal of Virological Methods*, 149:76-84 (2008); Kim, et. al., Rapid detection and identification of 12 respiratory viruses using a dual priming oligonucleotide system-based multiplex PCR assay, Journal of Virological Methods, doi:10.1016/j.jviromet.2008.11.007 (2008); Horii et. al., Use of dual priming oligonucleotide system to detect multiplex sexually transmitted pathogens in clinical specimens, Letters in Applied Microbiology, doi: 10.111/j.1472-765X2009.02618x(2009)). As such, the DPO has eventually two primer segments with distinct hybridization properties: the 5'-first priming portion that initiates stable hybridization, and the 3'-second priming portion that mainly determines target specificity.

The mDSO structure is a reversal of the DSO structure: the 5'-second priming portion (or the 5'-second hybridization portion) that mainly determines target specificity, and the 3'-first priming portion (or the 3'-first hybridization portion) that initiates stable hybridization.

According to a preferred embodiment, the universal base in the separation portion is selected from the group consisting of deoxyinosine, inosine, 7-deaza-2'-deoxyinosine, 2-aza-2'-deoxyinosine, 2'-OMe inosine, 2'-F inosine, deoxy 3-nitropyrrole, 3-nitropyrrole, 2'-OMe 3-nitropyrrole, 2'-F 3-nitropyrrole, 1-(2'-deoxy -beta-D-ribofuranosyl)-3-nitropyrrole, deoxy 5-nitroindole, 5-nitroindole, 2'-OMe 5-nitroindole, 2'-F 5-nitroindole, deoxy 4-nitrobenzimidazole, 4-nitrobenzimidazole, deoxy 4-aminobenzimidazole, 4-aminobenzimidazole, deoxy nebularine, 2'-F nebularine, 2'-F 4-nitrobenzimidazole, PNA-5-introindole, PNA-nebularine, PNA-inosine, PNA-4-nitrobenzimidazole, PNA-3-nitropyrrole, morpholino-5-nitroindole, morpholino-nebularine, morpholino-inosine, morpholino-4-nitrobenzimidazole, morpholino-3-nitropyrrole, phosphoramidate-5-nitroindole, phosphoramidate-nebularine, phosphoramidate-inosine, phosphoramidate-4-nitrobenzimidazole, phosphoramidate-3-nitropyrrole, 2'-0-methoxyethyl inosine, 2'0-methoxyethyl nebularine, 2'-0-methoxyethyl 5-nitroindole, 2'-0-methoxyethyl 4-nitro-benzimidazole, 2'-0-methoxyethyl 3-nitropyrrole, and combinations thereof. More preferably, the universal base is deoxyinosine, 1-(2'-deoxy-beta-D-ribofuranosyl)-3-nitropyrrole or 5-nitroindole, most preferably, deoxyinosine.

Preferably, the separation portion comprises contiguous nucleotides having at least three, more preferably at least four, most preferably at least five universal bases, preferably, deoxyinosine.

Preferably, in the DPO structure the 5'-first priming portion is longer than the 3'-second priming portion. The 5'-first priming portion is preferably 15-60 nucleotides, more preferably 15-40 nucleotides, still more preferably 15-25 nucleotides in length. It is preferable that the 3'-second priming portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length. According to a preferred embodiment, the $T_m$ of the 5'-first priming portion ranges from 40° C. to 80° C., more preferably 45° C. to 65° C. The $T_m$ of the 3'-second priming portion ranges preferably from 10° C. to 40° C. It is preferable that the $T_m$ of the separation portion ranges from 3° C. to 15° C.

Preferably, in the mDSO structure the 3'-first priming portion (or the 3'-first hybridization portion) is longer than the 5'-second priming portion (or the 5'-second hybridization portion). The 3'-first priming portion is preferably 15-60 nucleotides, more preferably 15-40 nucleotides, still more preferably 15-25 nucleotides in length. It is preferable that the 5'-second priming portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length.

According to a preferred embodiment, the $T_m$ of the 3'-first priming portion ranges from 40° C. to 80° C., more preferably 45° C. to 65° C. The $T_m$ of the 5'-second priming portion ranges preferably from 10° C. to 40° C. It is preferable that the $T_m$ of the separation portion ranges from 3° C. to 15° C.

According to a preferred embodiment, the labeled probe has a modified dual specificity oligonucleotide (mDSO) structure represented by the following general formula II:

$$5'-X'_p-Y'_q-Z'_r-3' \quad (II)$$

wherein, $X'_p$ represents a 5'-second priming portion (or the 5'-second hybridization portion) having a hybridizing nucleotide sequence complementary to the target nucleic acid sequence; $Y'_q$ represents a separation portion comprising at least three universal bases, $Z'_r$ represents a 3'-first priming portion (or a 3'-first hybridization portion) having a hybridizing nucleotide sequence complementary to the target nucleic acid sequence; p, q and r represent the number of nucleotides; and X', Y' and Z' are deoxyribonucleotides or ribonucleotides; the $T_m$ of the 5'-second priming portion (or the 5'-second hybridization portion) is lower than that of the 3'-first priming portion (or the 3'-first hybridization portion) and the separation portion has the lowest $T_m$ in the three portions of $X'_p$, $Y'_q$ and $Z'_r$; the separation portion separates the 5'-second priming portion (or the 5'-second hybridization portion) from the 3'-first priming portion (or the 3'-first hybridization portion) in terms of annealing events to the target nucleic acid sequence, the annealing specificity of the oligonucleotide are determined dually by the 5'-second priming portion (or the 5'-second hybridization portion) and the 3'-first priming portion (or the 3'-first hybridization portion) such that the overall annealing specificity of the probe is enhanced.

Preferably, in the mDSO structure for the labeled probe, the 3'-first priming portion (or the 3'-first hybridization portion) is longer than the 5'-second priming portion (or the 5'-second hybridization portion). The 3'-first priming portion is preferably 15-60 nucleotides, more preferably 15-40 nucleotides, still more preferably 15-25 nucleotides in length. It is preferable that the 5'-second priming portion is 3-15 nucleotides, more preferably 5-15 nucleotides, still more preferably 6-13 nucleotides in length. The separation portion is preferably 3-10 nucleotides, more preferably 4-8 nucleotides, most preferably 5-7 nucleotides in length.

According to a preferred embodiment, the $T_m$ of the 3'-first priming portion (or the 3'-first hybridization portion) ranges from 40° C. to 80° C., more preferably 45° C. to 65° C. The $T_m$ of the 5'-second priming portion (or the 5'-second hybridization portion) ranges preferably from 10° C. to 40° C. It is preferable that the $T_m$ of the separation portion ranges from 3° C. to 15° C.

According to a preferred embodiment, the upstream primer or the downstream primer has a dual priming oligonucleotide (DPO) structure represented by the following general formula I:

$$5'-X_p-Y_q-Z_r-3' \quad (I)$$

wherein, $X_p$ represents a 5'-first priming portion having a hybridizing nucleotide sequence complementary to the target nucleic acid; $Y_q$ represents a separation portion comprising at least three universal bases, $Z_r$ represents a 3'-second priming portion having a hybridizing nucleotide sequence complementary to the target nucleic acid; p, q and r represent the number of nucleotides, and X, Y, and Z are deoxyribonucleotides or ribonucleotides; the $T_m$ of the 5'-first priming portion is higher than that of the 3'-second priming portion and the separation portion has the lowest $T_m$ in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the upstream primer is enhanced.

According to a preferred embodiment, the primer (i.e., the counterpart primer) used together with the THD primer for target amplification has a dual priming oligonucleotide (DPO) structure represented by the following general formula I:

$$5'-X_p-Y_q-Z_r-3' \quad (I)$$

wherein, $X_p$ represents a 5'-first priming portion having a hybridizing nucleotide sequence complementary to the target nucleic acid; $Y_q$ represents a separation portion comprising at least three universal bases, $Z_r$ represents a 3'-second priming portion having a hybridizing nucleotide sequence complementary to the target nucleic acid; p, q and r represent the number of nucleotides, and X, Y, and Z are deoxyribonucleotides or ribonucleotides; the $T_m$ of the 5'-first priming portion is higher than that of the 3'-second priming portion and the separation portion has the lowest $T_m$ in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the primer is enhanced.

The conventional technologies using primers or probes for detecting target nucleic acid cannot be free from false signals at a satisfactory level due to inherent limitations of primers and probes used. However, the THD primer, the labeled probe, the upstream primer, the downstream primer and the reverse primer having the DPO or the mDSO structure with such intriguing design are hybridized with target nucleic acid sequences with a dramatically enhanced specificity, permitting to detect target nucleic acid sequences with no false signals.

As used herein, the term "conventional" in conjunction with primers or probes means any primer or probe not having DPO or mDSO structure. They are described herein as conventional primers or conventional probes.

Following the hybridization with the target nucleic acid sequence, the resultant of step (a) is contacted to the template-dependent nucleic acid polymerase having the 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained.

The phrase "under conditions for the 5'-cleavage reaction and the 3'-extension reaction of the THD primer by the template-dependent nucleic acid polymerase" means conditions sufficient to induce extension reaction at the 3'-end and cleavage reaction at the 5'-end or on the 5'-end portion of the THD primer by the template-dependent nucleic acid polymerase having the 5' to 3' nuclease activity. Such conditions may follow those for primer extension by conventional nucleic acid polymerases. For example, the conditions will be found in Joseph Sambrook, et al., *Molecular Cloning, A Laboratory Manual*, Cold Spring Harbor Laboratory Press, Cold Spring Harbor, N.Y.(2001). As illustrative example, the conditions include incubation of a target nucleic acid sequence, the THD primer, a thermostable DNA polymerase (e.g., Taq DNA polymerase), dNTPs and $MgCl_2$ at relatively high temperature (e.g., 50-75° C.) for a suitable period of time.

The phrase "under conditions for the 5'-cleavage reaction and the 3'-extension reaction of the two primers by the template-dependent nucleic acid polymerase" means conditions sufficient to induce extension reaction at the 3'-end and cleavage reaction at the 5'-end or on the 5'-end portion of the primer pair (a forward primer and a reverse primer) capable of target amplification by the template-dependent nucleic acid polymerase having the 5' to 3' nuclease activity. The details of conditions will be described with reference to the phrase indicated above.

According to a preferred embodiment, the template-dependent nucleic acid polymerase having the 5' to 3' nuclease activity is a thermostable DNA polymerase which may be obtained from a variety of bacterial species, including *Thermus aquaticus* (Taq), *Thermus thermophilus* (Tth), *Thermus filiformis, Thermis flavus, Thermococcus literalis, Pyrococcus furiosus* (Pfu), *Thermus antranikianii, Thermus caldophllus, Thermus chliarophllus, Thermus flavus, Thermus igniterrae, Thermus lacteus, Thermus oshimai, Thermus ruber, Thermus rubens, Thermus scotoductus, Thermus silvans, Thermus* species Z05, *Thermus* species sps 17, *Thermus thermophilus, Thermotoga maritima, Thermotoga neapolitana* and *Thermosipho africanus*. Most preferably, the template-dependent nucleic acid polymerase having the 5' to 3' nuclease activity is Taq DNA polymerase.

Finally, the signal indicative of the presence of the target nucleic acid sequence is detected. The signal detection may be performed for each cycle of the repetition, at the end of the repetition or at each of predetermined time intervals during the repetition. Preferably, the signal detection may be performed for each cycle of the repetition to improve the detection accuracy.

The present invention does not require any particular sequence or length of the target nucleic acid sequences to be detected and/or amplified. The RNA target sequence should be reverse-transcribed to cDNA (Joseph Sambrook, et al., *Molecular Cloning, A Laboratory Manual*, Cold Spring Harbor Laboratory Press, Cold Spring Harbor, N.Y.(2001); and Noonan, K. F. et al., *Nucleic Acids Res.* 16:10366 (1988)). In particular, target nucleic acid sequences which may be detected and/or amplified include any naturally occurring procaryotic, eukaryotic (for example, protozoans and parasites, fungi, yeast, higher plants, lower and higher animals, including mammals and humans) or viral (for example, Herpes viruses, HIV, influenza virus, Epstein-Barr virus, hepatitis virus, polio virus, etc.) or viroid nucleic acid.

The THD primer hybridized with the target nucleic acid sequence is cleaved by the template-dependent nucleic acid polymerase having the 5' to 3' nuclease activity, and the label linked to the THD primer is released to generate a signal indicative of the presence of the target nucleic acid sequence. The signal may be detected or measured by conventional methods for each label. For example, where the label is with an enzyme, the signal is detected using a substrate for the enzyme. Where gold particles as a metal label are used, the signal is detected by a silver staining method using silver nitrate. The fluorescence signal may be detected or measured by conventional methods, e.g., fluorometers.

The signal detected may be obtained directly from the label per se or indirectly from a successive label-involving reaction. Also, the signal detected may be obtained from a label released or a label remained (not included in cleaved nucleotides) (e.g., interactive labeling system).

The advantages of the present invention become more prominent as at least two target nucleic acid sequences are simultaneously detected. According to the present invention, a multitude of target nucleic acid sequences can be simultaneously detected on a reaction.

Furthermore, the present invention is very useful in detection of a nucleotide variation. The term "nucleotide variation" used herein refers to a nucleotide polymorphism in a DNA sequence at a particular location among contiguous DNA segments that are otherwise similar in sequence. Such contiguous DNA segments include a gene or any other portion of a chromosome. For example, the nucleotide variation detected in the present invention includes deletion, insertion and substitution. Exemplified nucleotide variation includes numerous variations in a human genome (e.g., variations in the MTHFR (methylenetetrahydrofolate reductase) gene), variations involved in drug resistance of pathogens and tumorigenesis-causing variations.

Preferably, the nucleotide variation detected in this invention is a base substitution, more preferably, SNP (single nucleotide polymorphism) and point mutation.

In another aspect of this invention, there is provided a kit for detecting a target nucleic acid sequence from a DNA or a mixture of nucleic acids using a 5'-cleavage reaction and a 3'-extension reaction of a target hybridization and detection primer (THD primer), which comprises:

(a) the THD primer comprising (i) a hybridizing nucleotide sequence complementary to the target nucleic acid sequence and (ii) a label or an interactive label system containing a plurality of labels; and (b) a template-dependent nucleic acid polymerase having a 5' to 3' nuclease activity;

wherein when the THD primer is hybridized with the target nucleic acid sequence, the THD primer is extended by the polymerase activity of the nucleic acid polymerase and the THD primer is cleaved by 5' to 3' nuclease activity of the nucleic acid polymerase to release the label or at least one label of the interactive label system from the THD primer, whereby a signal indicative of the presence of the target nucleic acid sequence is obtained.

According to a preferable embodiment, the kit further comprises an additional primer for target amplification together with the THD primer, an upstream primer, a downstream primer, a labeled probe or combinations thereof.

According to a preferable embodiment, the additional primer for target amplification, the upstream primer, and/or the downstream primer has a label.

The label useful in the primers or the labeled probe will be described as that in the THD primer. Preferably, the label is a FRET label.

The labeled probe and the primers labeled are also cleaved by the template-dependent nucleic acid polymerase having the 5' to 3' nuclease activity to release the label from them, giving two separate signals indicative of the presence of the target nucleic acid sequence.

Since the kit of this invention is constructed to perform the detection method of the present invention described above, the common descriptions between them are omitted in order to avoid undue redundancy leading to the complexity of this specification.

The present kits may optionally include the reagents required for performing target amplification PCR reactions (e.g., PCR reactions) such as buffers, DNA polymerase cofactors, and deoxyribonucleotide-5-triphosphates. Optionally, the kits may also include various polynucleotide molecules, reverse transcriptase, various buffers and reagents, and antibodies that inhibit DNA polymerase activity.

The kits may also include reagents necessary for performing positive and negative control reactions. Optimal amounts of reagents to be used in a given reaction can be readily determined by the skilled artisan having the benefit of the current disclosure. The kits, typically, are adapted to contain in separate packaging or compartments the constituents afore-described.

The features and advantages of the present invention will be summarized as follows:

(a) The conventional real-time PCR methods require labeled probes or complicatedly modified primer structure such as a hairpin structure, which make the design, synthesis or sequence selection of the probe and primer difficult. However, since the THD primer of the present invention is used for not only target amplification but also signal amplification without additional labeled probes or complicatedly modified primer structure, the design, synthesis or sequence selection of the THD primer for real-time PCR is relatively simple and easy.

(b) Optimization of the conventional real-time PCR methods is difficult because it is necessary for the conventional real-time PCR reactions that hybridization conditions be optimized for probes as well as primers. Conventional real-time PCR methods using primers with tails to form hairpin loops are supposed to optimize reaction conditions with considering formation and deformation of hairpin loops in primers. However, the present invention could completely be free from the troublesome matters and shortcomings associated with the optimization of the conventional real-time PCR methods.

(c) As addressed in Example 7, various combinations of (i) the THD primers as a forward primer, a reverse primer or an upstream primer, or (ii) the THD primers and probes permit to effectively detect target nucleic acid sequences.

(d) The conventional real-time PCR methods are very unlikely to adopt to multiplex assay due to the difficulty of primer or probe design and optimization. In contrast, since the present invention uses only a labeled primer without additional probes or complicatedly modified primer structure in real-time PCR, it is possible to exhibit excellent real-time target detection in multiplex manner.

(e) Compared to the conventional real-time PCR probe, the THD primer is extended during the process and in turn the extended THD primer shows higher binding strength to target nucleic acid sequences. The conventional real-time PCR primer requires complicatedly modified structure such as a hairpin loop which bothers the binding to the target nucleic acid sequence. In contrast, the THD primer does not require such modification so that the THD primer has better binding efficiency to target nucleic acid sequences. This feature is responsible in part for enhanced target detection efficiency of the present method.

(f) The present method can readily perform real-time PCR reactions using primers that are generally used for PCR reactions. In short, primers to generate amplicons in PCR reactions can secure a successful real-time PCR reaction. In this regard, the present method is considered to be time- and cost-effective in the development of a real-time PCR assay.

(g) As discussed hereinabove, the primer and/or probe used in the present invention having the DPO or mDSO structure gives rise to the improvement of binding specificity, thereby eliminating false positive signals associated with non-target binding of the primer and/or probe in real-time PCR reaction.

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Evaluation of the THD Primer in the Detection of a Target Nucleic Acid

The THD primer of this invention was evaluated whether the dual-labeled THD primer can generate a signal sufficient to detect a target nucleic acid sequence when the THD primer anneals to the target nucleic acid sequence under Taq DNA polymerase reaction and the 5'-cleavage reaction and the 3'-extension reaction of the THD primer is conducted by a template-dependent nucleic acid polymerase having a 5' to 3' nuclease activity to separate the fluorescent reporter molecule from the quencher molecule positioned on the THD primer. The THD primer is dual-labeled with 6-FAM (6-carboxyfluoresceine) as a reporter molecule and the Black Hole Quencher 1 (BHQ-1) as a quencher molecule. The positions of the labels are indicated in the oligonucleotide sequence.

To test this evaluation, we used *Staphylococcus aureus* gene as a target template and for experimental convenience, the synthetic oligonucleotide was used as a template for *S. aureus* gene. The signal was measured at a predetermined time interval without the amplification of the target nucleic acid sequence.

The process and results for the generation of signal and detection of target *Staphylococcus aureus* gene are described herein.

The sequences of the synthetic template and the dual-labeled THD primer used in this EXAMPLE are:

SA-Tem
(SEQ ID NO: 1)
5'-gccaataaaactaggaggaaatttaaatgttagaatttgaacaaggatttaatcatttagcgactttaaaggtcattggtgtaggtggtggcggtaacaacgccgtaaaccgaatgattgaccacggaatgaataatgttgaatttatcgctatcaacacagacggtcaagctttaaacttatctaaagctgaatctaaa-3';
and SA-THD
(SEQ ID NO: 2)
5'-[6-FAM]CATTCCG[BHQ1-dT]GGTCAATCATTCGGTT-3'.

The 5'-cleavage reaction and the 3'-extension reaction of the dual-labeled THD primer were conducted in the final volume of 20 μl containing 2 pmole of template (SEQ ID NO: 1), 10 μl of 2× master mix containing 10 mM MgCl$_2$, 2 units of Taq DNA polymerase (Solgent, Korea), 200 μM each of four dNTPs (dATP, dCTP, dGTP and dTTP) and 5 pmole of dual-labeled THD primer (SEQ ID NO: 2); the tube containing the reaction mixture was placed in the real-time thermocycler (CFX96, Bio-Rad); the reaction mixture was denatured for 10 min at 95° C. and subjected to 40 cycles of 60 sec at 55° C. or 65° C. Detection of the generated signal was performed at each cycle by the predetermined time interval.

As shown in FIG. 5, even in the reaction where there is no amplification of target nucleic acid sequence, the increase in florescent signal on *Staphylococcus aureus* was observed on the real time basis, by monitoring the florescent signal at the predetermined time interval. Additionally, no difference was shown in the signal between 55° C. (No. 2) and 65° C. (No. 4). No change in the florescent signal was observed in the absence of templates (No. 1 and 3).

Example 2

Examination of the THD Primer Under the Conditions of Real-Time PCR Reaction for the Detection of a Target Nucleic Acid We further examined whether the THD primer can generate a signal sufficient to detect a target nucleic acid sequence when the repetition of denaturation, hybridization, cleavage and extension was applied at the various concentration of dNTPs under the conditions of real-time PCR reaction.

To examine this evaluation, the same template (SEQ ID NO: 1) and the dual-labeled THD primer (SEQ ID NO: 2) used in EXAMPLE 1 are used for the real-time target signal amplification.

The real-time target signal amplification was conducted at the various concentration of dNTPs (final concentration of 500 μM, 200 μM, 20 μM or 0 μM) in the final volume of 20 μl containing 2 pmole of template (SEQ ID NO: 1), 10 μl of 2× master mix containing 10 mM MgCl$_2$, 2 units of Taq DNA polymerase (Solgent, Korea) and 5 pmole of dual-labeled THD primer (SEQ ID NO: 2); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 55° C. and 90 sec at 72° C. Detection of the generated signal was performed at the extension step (72° C.) of each cycle.

As shown in FIG. 6, no florescent signal amplification of the target nucleic acid sequence was observed in the negative control reactions where there was no Taq polymerase (No. 1) or template (No. 2). Such results indicate that there was no signal amplification either by hybridization of target template and the THD primer or by the cleavage of the single stranded THD primer itself. On the other hand, the florescent signal of the target nucleic acid sequence was observed not only in the absence of dNTPs (No. 6) but also under the different concentration of dNTPs (No. 3, 4 and 5). With 500 μM of dNTPs, the Ct value was the highest and the signal intensity was the lowest (No. 3) where 20 μM of dNTPs showed the lowest Ct value and the highest signal intensity (No. 5).

Therefore, without the amplification of target nucleic acid sequence, the repetition of denaturation, hybridization, cleavage and extension using the THD primer was sufficient to generate the target florescent signal, hence it enables the detection of the target nucleic acid sequence by real-time signal amplification.

Example 3

Differences Between THD Primer and Probe in Real-Time PCR Amplification

The main differences between primer and probe are that the probe is not incorporated into the amplification product. To confirm that the THD primer is incorporated into the real-time PCR amplification product but the probe is not under the real-time PCR conditions, the real-time PCR was conducted for detecting *Streptococcus pneumoniae* gene and *Neisseria meningitidis* gene using the THD primer as a forward primer.

When the target nucleic acid sequence of the *S. pneumoniae* gene is used as a template, the sequences of the dual-labeled THD primer as a forward primer, the reverse primer and the dual-labeled probe used in this EXAMPLE are:

SP-THD
(SEQ ID NO: 4)
5'-[6-FAM]TCCTTCAAACTGTGGATT[BHQ1-dT]GGGTGT-3'

SP-Probe
(SEQ ID NO: 5)
5'-[6-FAM]TCCTTCAAACTGTGGATT[BHQ1-dT]GGGTGT[PhosQ]-3'

SP-P2
(SEQ ID NO: 6)
5'-GGTTTCCGTACAGCCTTGA-3'

Real-time PCR was conducted in the final volume of 20 μl containing 10 ng of genomic DNA of *S. pneumoniae*, 10 μl of 2× QIAGEN Multiplex Master Mix containing 6 mM MgCl$_2$, Taq DNA polymerase and dNTPs (QIAGEN), 10 pmole of dual-labeled THD primer (SEQ ID NO: 4) or dual-labeled probe (SEQ ID NO: 5), and 10 pmole of reverse primer (SEQ ID NO: 6); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle. The amplified PCR products were separated in 2% agarose gel stained with ethidium bromide.

Figure 7B:
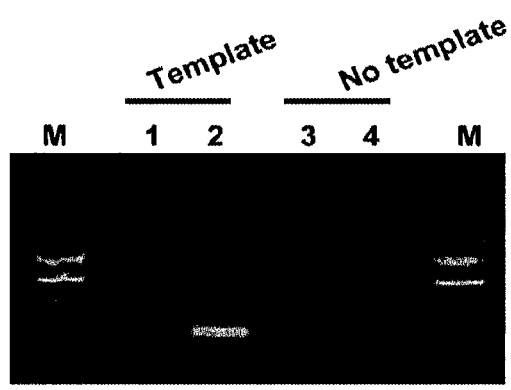
FIG. 7B is an agarose gel photograph showing the results of the real-time PCR amplification.

As shown in FIG. 7, the THD primer in real-time PCR makes it possible to obtain the products from the amplification of target nucleic acid sequence as well as the amplification of target signal (No. 3 of FIG. 7A), and the products from the amplified target nucleic acid sequence, *S. pneumoniae*, were confirmed on agarose gel (Lane 2 of FIG. 7B). On the other hand, there was no change in the florescent signal in real-time PCR using dual-labeled probe (No. 1 of FIG. 7A) unlike the THD primer, and there was also no products observed on agarose gel (Lane 1 of FIG. 7B).

When the target nucleic acid sequence of the *N. meningitidis* gene is used as a template, the sequences of the dual-labeled THD primer as a forward primer, the reverse primer and the dual-labeled probe used in this EXAMPLE are:

```
NM-THD2
                                         (SEQ ID NO: 8)
5'-[6-FAM]TCCACCAATGGCG[BHQ1-dT]ATAGCGGA-3'

NM-Probe
                                         (SEQ ID NO: 9)
5'-[6-FAM]TCCACCAATGGCGTATAGCGGA[BHQ1a-Q]-3'

NM-P1
                                        (SEQ ID NO: 10)
5'-CCAATCCCTATACCTTTACGTC-3'
```

Real-time PCR was conducted in the final volume of 20 μl containing 10 ng of genomic DNA of *S. pneumoniae*, 10 μl of 2× QIAGEN Multiplex Master Mix containing 6 mM MgCl$_2$, Taq DNA polymerase and dNTPs (QIAGEN), 10 pmole of dual-labeled THD primer (SEQ ID NO: 8) or dual-labeled probe (SEQ ID NO: 9), and 10 pmole of reverse primer (SEQ ID NO: 10); the tube containing the reaction mixture was placed in the Real-Time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle. The amplified PCR products were separated in 2% agarose gel stained with ethidium bromide.

Figure 8B:
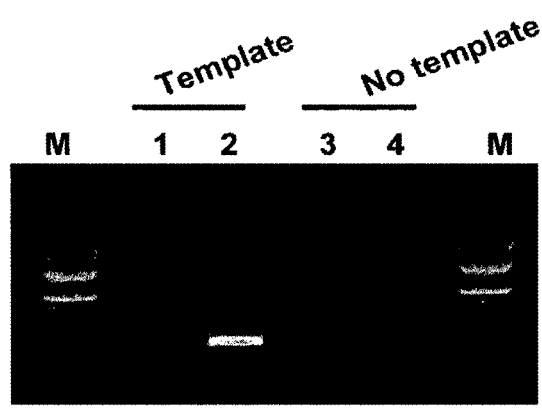
FIG. 8B is an agarose gel photograph showing the results of the real-time PCR amplification.

Real-time PCR amplification for *N. meningitidis* gene as a target nucleic acid showed the similar results as shown in FIG. 7. The results of real-time PCR using the THD primer showed the amplification of target nucleic acid sequence as well as the amplification of the target signal (No. 3 of FIG. 8A), and the PCR products of *N. meningitidis* gene was detected on agarose gel (Lane 2 of FIG. 8B). However, there was no change in the florescent signal in the real-time PCR using dual-labeled probe (No. 1 of FIG. 8A), and there was also no products of target nucleic acid sequence shown on the agarose gel (Lane 1 of FIG. 8B).

Example 4

Real-Time PCR Specificity Using the THD Primer

The real-time PCR specificity using the THD primer was tested by detecting the target nucleic acid sequences of *S. pneumoniae* gene and *N. meningitidis* gene. For this study, the dual-labeled THD primer was used as a forward primer in the real-time PCR amplification.

A. Real-Time PCR Specificity for *S. pneumoniae*

The sequences of the dual-labeled THD primer and the reverse primer used in this EXAMPLE are:

```
SP-THD
                                         (SEQ ID NO: 4)
5'-[6-FAM]TCCTTCAAACTGTGGATT[BHQ1-dT]GGGTGT-3'

SP-P2
                                         (SEQ ID NO: 6)
5'-GGTTTCCGTACAGCCTTGA-3'
```

Real-time PCR was conducted in the final volume of 20 μl containing 1 ng of genomic DNA of *S. pneumoniae*, *N. meningitidis* or *N. gonorrhoeae*, 10 μl of 2× QIAGEN Multiplex Master Mix containing 6 mM MgCl$_2$, Taq DNA polymerase and dNTPs (QIAGEN), 10 pmole of dual-labeled THD primer (SEQ ID NO: 4) and 10 pmole of reverse primer (SEQ ID NO: 6); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle.

Figure 9:
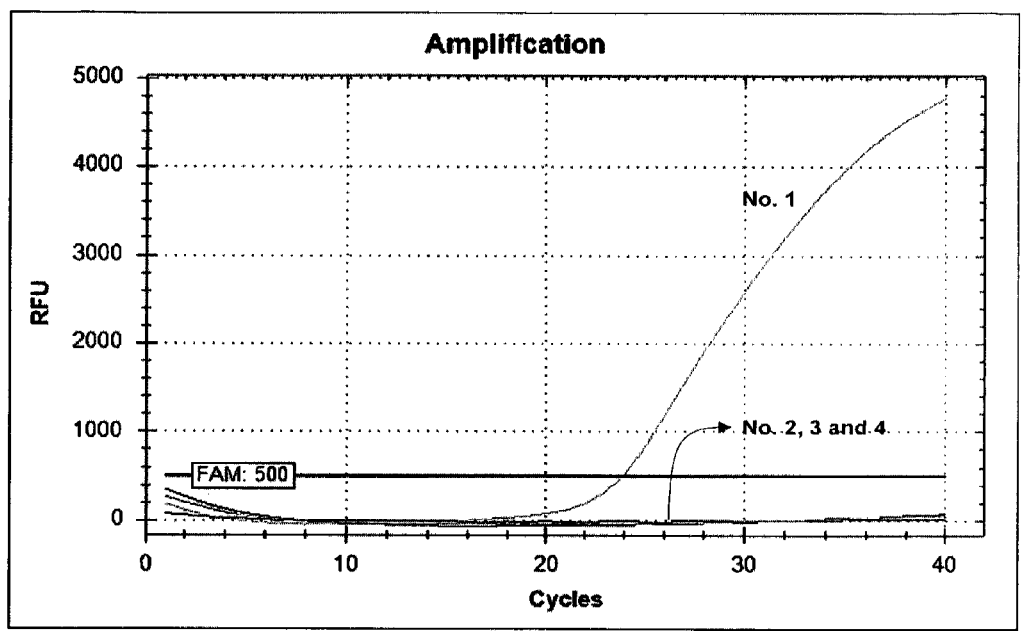
FIG. 9 shows the real-time PCR specificity for *Streptococcus pneumoniae* (SP) gene using a THD primer as a forward primer in the real-time PCR amplification.

In real-time PCR using *S. pneumoniae* gene as a target nucleic acid, florescent signal amplification occurred (No. 1 of FIG. 9), whereas there was no florescent signal amplification observed in the real-time PCR with non-target nucleic acid sequences such as *N. gonorrhoeae* (No. 2 of FIG. 9) and *N. meningitidis* (No. 3 of FIG. 9) as well as the negative control (No. 4 of FIG. 9).

B. Real-Time PCR Specificity for *N. meningitidis*

The sequences of the dual-labeled THD primer and the reverse primer used in this EXAMPLE are:

```
NM-THD1
                                         (SEQ ID NO: 7)
5'-[6-FAM]CCATAACC[BHQ1-dT]TGAGCAATCCAIIIIICCTGACG
TTC-3'

NM-P1
                                        (SEQ ID NO: 10)
5'-CCAATCCCTATACCTTTACGTC-3'
```

Real-time PCR was conducted in the final volume of 20 μl containing 1 ng of genomic DNA of *S. pneumoniae*, *N. meningitidis* or *N. gonorrhoeae*, 10 μl of 2× QIAGEN Multiplex Master Mix containing 6 mM MgCl$_2$, Taq DNA polymerase and dNTPs (QIAGEN), 10 pmole of dual-labeled THD primer (SEQ ID NO: 7) and 10 pmole of reverse primer (SEQ ID NO: 10); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle.

Figure 10:
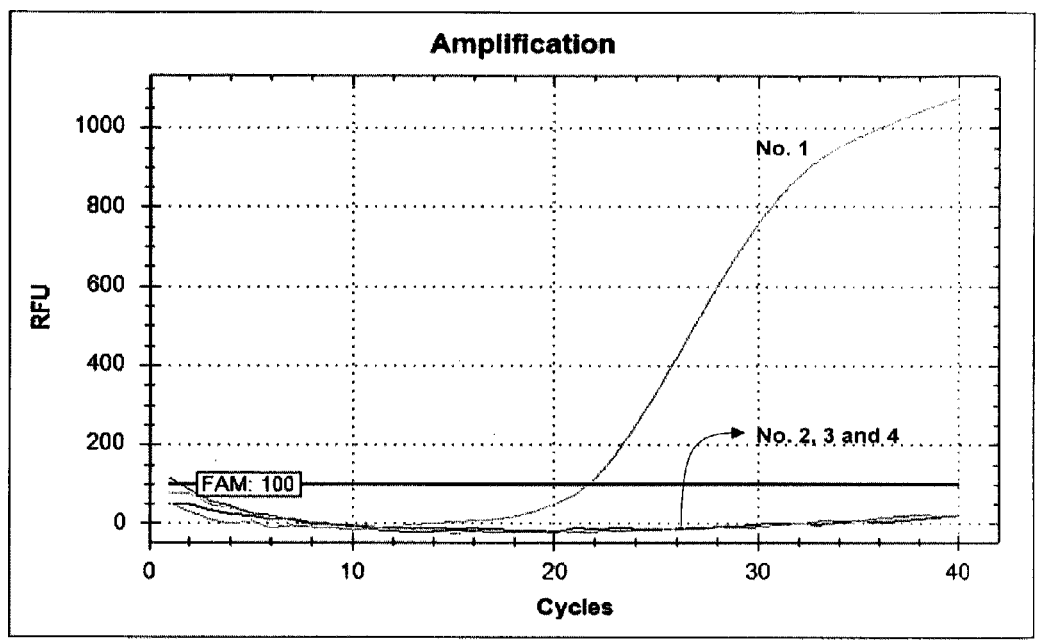
FIG. 10 shows the real-time PCR specificity for *Neisseria meningitides* (NM) gene using a THD primer as a forward primer in the real-time PCR amplification.

In real-time PCR using *N. meningitidis* gene as a target nucleic acid, florescent signal amplification occurred (No. 1 of FIG. 10), whereas there was no florescent signal amplification observed in the real-time PCR with non-target nucleic acid sequences such as *N. gonorrhoeae* (No. 2 of FIG. 10) and *S. pneumoniae* (No. 3 of is FIG. 10) as well as the negative control (No. 4 of FIG. 10).

Example 5

Real-Time PCR Sensitivity Using the THD Primer

The real-time PCR sensitivity using the THD primer was tested by detecting the target nucleic acid sequences of *S. pneumoniae* gene and *N. meningitidis* gene. For this study, the dual-labeled THD primer was used as a forward primer in the real-time PCR amplification.

A. Real-time PCR sensitivity for *S. pneumoniae*

The sequences of the dual-labeled THD primer and the reverse primer used in this EXAMPLE are:

```
SP-THD
                                         (SEQ ID NO: 4)
5'-[6-FAM]TCCTTCAAACTGTGGATT[BHQ1-dT]GGGTGT-3'

SP-P2
                                         (SEQ ID NO: 6)
5'-GGTTTCCGTACAGCCTTGA-3'
```

Real-time PCR was conducted in the final volume of 20 μl containing of the serial diluted genomic DNA of *S. pneumoniae* (10 ng, 1 ng, 100 pg, 10 pg, 1 pg or 0.1 pg), 10 μl of 2× QIAGEN Multiplex Master Mix containing 6 mM $MgCl_2$, Taq DNA polymerase and dNTPs (QIAGEN), 10 pmole of dual-labeled THD primer (SEQ ID NO: 4) and 10 pmole of reverse primer (SEQ ID NO: 6); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle.

Figure 11:
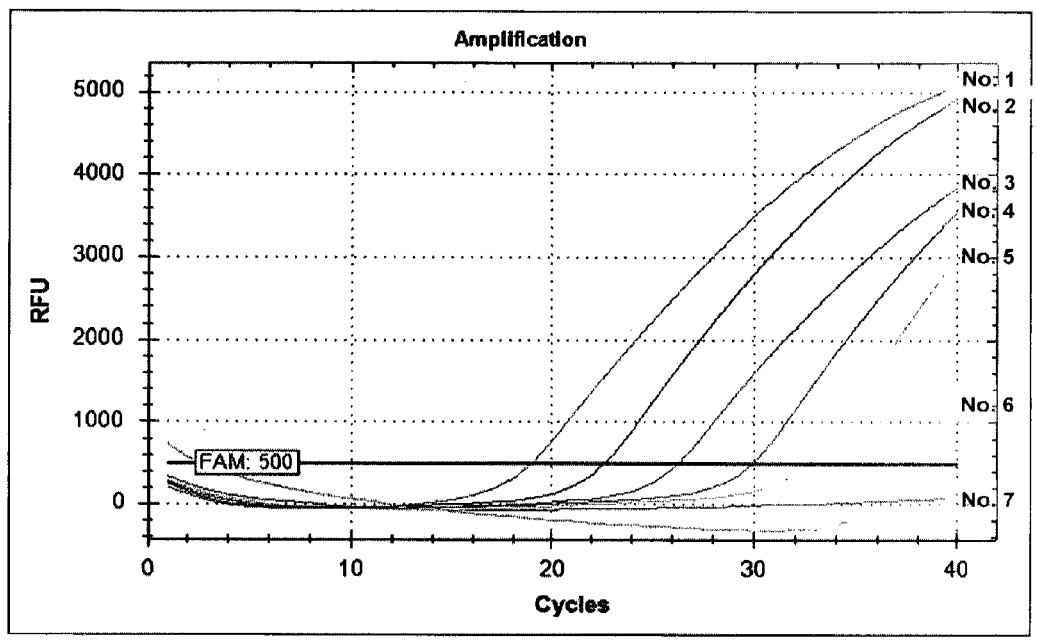
FIG. 11 shows the real-time PCR sensitivity for *Streptococcus pneumoniae* (SP) gene using a THD primer as a forward primer in the real-time PCR amplification.

As shown in FIG. 11, when real-time PCR was performed using *S. pneumoniae* genomic DNA after the serial dilution starting from 10 ng, it could detect target nucleic acid sequence up to 0.1 pg (No. 1-6).

B. Real-Time PCR Sensitivity for *N. meningitidis*

The sequences of the dual-labeled THD primer and the reverse primer used in this EXAMPLE are:

```
NM-THD1
                                         (SEQ ID NO: 7)
5'-[6-FAM]CCATAACC[BHQ1-dT]TGAGCAATCCAIIIIICCTGACG
TTC-3'

NM-P1
                                         (SEQ ID NO: 10)
5'-CCAATCCCTATACCTTTACGTC-3'
```

Real-time PCR was conducted in the final volume of 20 μl containing of the serial diluted genomic DNA of *N. meningitidis* (10 ng, 1 ng, 100 pg, 10 pg, 1 pg or 0.1 pg), 10 μl of 2× QIAGEN Multiplex Master Mix containing 6 mM $MgCl_2$, Taq DNA polymerase and dNTPs (QIAGEN), 10 pmole of dual-labeled THD primer (SEQ ID NO: 7) and 10 pmole of reverse primer (SEQ ID NO: 10); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle.

Figure 12:
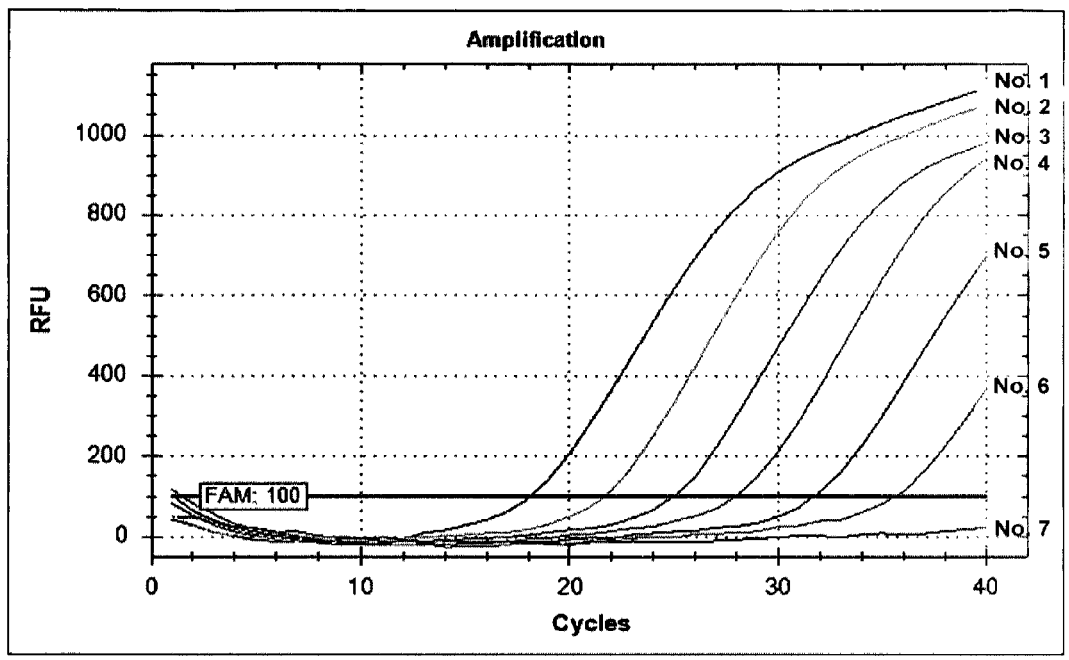
FIG. 12 shows the real-time PCR sensitivity for *Neisseria meningitides* (NM) gene using a THD primer as a forward primer in the real-time PCR amplification.

As shown in FIG. 12, when real-time PCR was performed using *N. meningitidis* genomic DNA after the serial dilution starting from 10 ng, it could detect target nucleic acid sequence up to 0.1 pg (No. 1-6).

Example 6

Nested Real-Time PCR Using the THD Primer

The specificity and sensitivity of the nested real-time PCR using the THD primer were further tested by detecting the target nucleic acid sequences of *S. pneumoniae* gene. For this study, the dual-labeled THD primer was used as a forward primer in the real-time PCR amplification.

A. Specificity of Nested Real-Time PCR

The sequences of the forward primer and the reverse primer for the first round of PCR and the sequence of the dual-labeled THD primer for the nested real-time PCR used in this EXAMPLE are:

```
SP-P1
                                         (SEQ ID NO: 3)
5'-TTGACCACTTCGCTATTTCC-3'

SP-THD
                                         (SEQ ID NO: 4)
5'-[6-FAM]TCCTTCAAACTGTGGATT/BHQ1-dT/GGGTGT-3'

SP-P2
                                         (SEQ ID NO: 6)
5'-GGTTTCCGTACAGCCTTGA-3'
```

The first round of PCR amplification was conducted in the final volume of 20 μl containing 10 ng of genomic DNA of *S. pneumoniae*, *N. meningitidis* or *N. gonorrhoeae*, 10 μl of 2× QIAGEN Multiplex Master Mix containing 6 mM $MgCl_2$, Taq DNA polymerase and dNTPs (QIAGEN), 10 pmole of forward primer (SEQ ID NO: 3) and 10 pmole of reverse primer (SEQ ID NO: 6); the tube containing the reaction mixture was placed in the thermal cycler (ABI9700, ABI); the reaction mixture was denatured for 10 min at 95° C. and subjected to 30 cycles of 30 sec at 94° C., 90 sec at 60° C. and 90 sec at 72° C.

The nested real-time PCR was conducted in the final volume of 20 μl containing 2 μl of the first round PCR product, 10 μl of 2× QIAGEN Multiplex Master Mix containing 6 mM $MgCl_2$, Taq DNA polymerase and dNTPs (QIAGEN), 5 pmole of dual-labeled THD primer (SEQ ID NO: 4), and 5 pmole of reverse primer (SEQ ID NO: 6); the tube containing the reaction mixture was placed in the real-time thermocycler (CFX96, Bio-Rad); the reaction mixture was denatured for 10 min at 95° C. and subjected to 20 cycles of 30 sec at 94° C., 90 sec at 60° C. and 90 sec at 72° C. Detection of the generated signal was performed at the extension step (72° C.) of each cycle.

Figure 13:
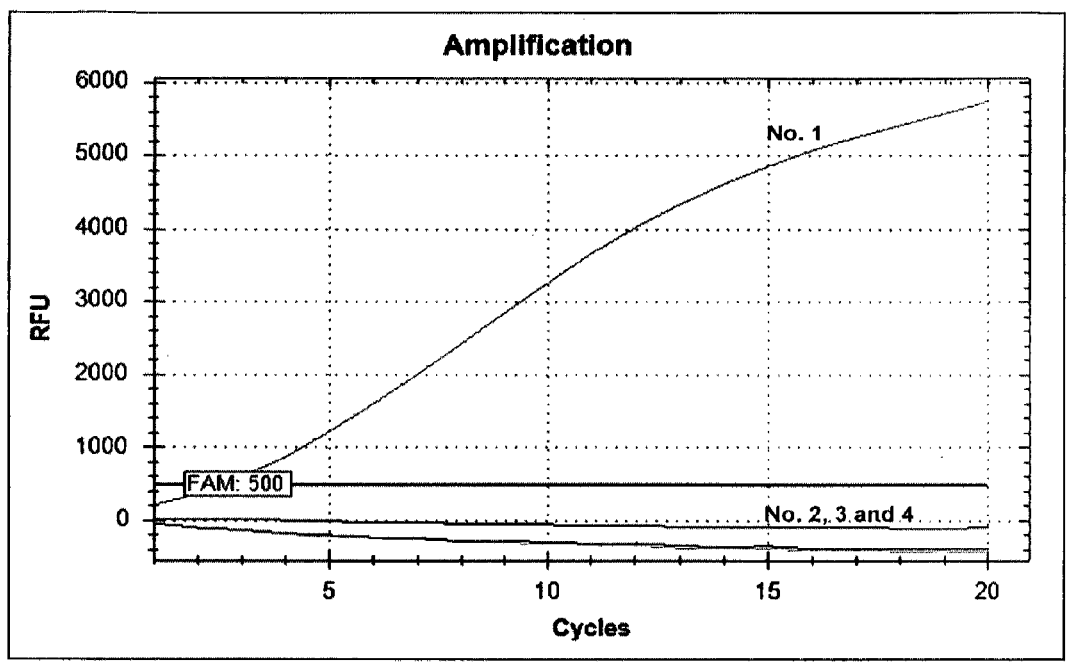
FIG. 13 shows the real-time PCR specificity for *Streptococcus pneumoniae* (SP) gene using a THD primer as a forward primer in the nested real-time PCR amplification.

As shown in the FIG. 13, there was a signal observed for real-time PCR on target nucleic acid, *S. pneumoniae* (No. 1), but there was no signal with non-target nucleic acid, *N. gonorrhoeae* (No. 2) and *N. meningitides* (No. 3), and with no template as a negative control (No. 4).

B. Sensitivity of Nested Real-Time PCR

The forward primer, reverse primer and dual-labeled THD primer sequences used in the EXAMPLE is:

The same sequences of the forward primer and the reverse primer for the first round of PCR and the sequence of the dual-labeled THD primer for the nested real-time PCR used in the EXAMPLE 6A for the specificity of the nested real-time PCR are used.

The first round of PCR amplification was conducted in the final volume of 20 μl containing the serial diluted genomic DNA of *S. pneumoniae* (10 ng, 1 ng, 100 pg, 10 pg, 1 pg, 100 fg, 10 fg or 1 fg), 10 μl of 2× QIAGEN Multiplex Master Mix containing 6 mM $MgCl_2$, Taq DNA polymerase and dNTPs (QIAGEN), 10 pmole of forward primer (SEQ ID NO: 3) and 10 pmole of reverse primer (SEQ ID NO: 6); the tube containing the reaction mixture was placed in the thermal cycler (ABI9700, ABI); the reaction mixture was denatured for 10 min at 95° C. and subjected to 30 cycles of 30 sec at 94° C., 90 sec at 60° C. and 90 sec at 72° C.

The nested real-time PCR was conducted in the final volume of 20 µl containing 2 µl of the PCR product, 10 µl of 2× QIAGEN Multiplex Master Mix containing 6 mM MgCl$_2$, Taq DNA polymerase and dNTPs (QIAGEN), 5 pmole of dual-labeled THD primer (SEQ ID NO: 4), and 5 pmole of reverse primer (SEQ ID NO: 6); the tube containing the reaction mixture was placed in the real-time thermocycler (CFX96, Bio-Rad); the reaction mixture was denatured for 10 min at 95° C. and subjected to 20 cycles of 30 sec at 94° C., 90 sec at 60° C. and 90 sec at 72° C. Detection of the generated signal was performed at the extension step (72° C.) of each cycle.

As shown in FIG. 14, target nucleic acid sequence was detected up to 10 fg of genomic DNA concentration (No. 1-7) when real-time PCR was done with the serially diluted *S. pneumoniae* genomic DNA as target template starting from 10 ng.

Example 7

Real-Time PCR Using the Various Combinations of the THD Primer

It is a first report discovered by the present invention that a general primer without any structural modifications such as a hairpin stem in molecular beacon, Sunrise or Scorpion can be used in real-time PCR with a dual function: a first function is the synthesis of complementary sequence and a second function is the generation of signals indicating a target nucleotide sequence. Thus, we applied the various combinations of the THD primer in real-time PCR amplifications, which is one of the main advantages of the THD primer.

For this study, the *N. gonorrhoeae* gene was used a target nucleic acid template. The THD primer has a DPO structure or a conventional structure with a dual label.

The sequences of the dual-labeled THD primers and primers used in this EXAMPLE are:

NG-P1
(SEQ ID NO: 11)
5'-CAATGGATCGGTATCACTCGCIIIIICGAGCAAGAAC-3'

NG-THD1
(SEQ ID NO: 12)
5'-[6-FAM]CAATGGATCGG[BHQ1-dT]ATCACTCGCIIIIICGAGCA
AGAAC-3'

NG-P2
(SEQ ID NO: 13)
5'-ATTGGCGTGTTTCGCATATTTAAG-3'

NG-THD2
(SEQ ID NO: 14)
5'-[6-FAM]ATTGGCGTGTTTCGCATA[BHQ1-dT]TTAAG-3'

NG-Probe
(SEQ ID NO: 15)
5'-[6-FAM]ATTGGCGTGTTTCGCATA[BHQ1-dT]TTAAG[Phos-Q]-3'

NG-P3
(SEQ ID NO: 16)
5'-TACGCCTGCTACTTTCACGCTIIIIIGTAATCAGATG-3'

NG-THD3
(SEQ ID NO: 17)
5'-[6-FAM]TACGCCTGCTAC[BHQ1-dT]TTCACGCTIIIIIGTAATC
AGATG-3'

A. Combinations of the Dual-Labeled THD Primer as a Forward Primer, a Reverse Primer or Both Real-time PCR was conducted in the final volume of 20 µl containing 1 ng of genomic DNA of *N. gonorrhoeae,* 10 µl of 2× QIAGEN Multiplex Master Mix containing 6 mM MgCl$_2$, Tag DNA polymerase and dNTPs (QIAGEN), 10 pmole of dual-labeled THD primer as a forward primer (SEQ ID NO: 12), reverse primer (SEQ ID NO: 17), or both (SEQ ID NO: 12 and 17) and 10 pmole of primer as a forward primer (SEQ ID NO: 11) or reverse primer (SEQ ID NO: 16); the tube containing the reaction mixture was placed in the real-time thermocycler (CFX96, Bio-Rad); the reaction mixture was denatured for 10 min at 95° C. and subjected to 40 cycles of 30 sec at 94° C., 90 sec at 60° C. and 90 sec at 72° C. Detection of the generated signal was performed at the extension step (72° C.) of each cycle.

B. Combinations of the Dual-Labeled THD Primer with a Dual-Labeled Internal Probe The combinations of the dual-labeled THD primer and the real-time PCR reaction were the same used in the EXAMPLE 7A except the use of the dual-labeled internal probe (5 pmole, SEQ ID NO: 15).

C. Combinations of the Dual-Labeled THD Primer as a Forward Primer and a Reverse Primer and/or an Unstream Primer The real-time PCR reaction was the same used in the EXAMPLE 7A except the use of the dual-labeled THD primer as a forward primer (5 pmole, SEQ ID NO: 14) and the use of the upstream dual-labeled THD primer (10 pmole, SEQ ID NO: 12) or the upstream primer (10 pmole, SEQ ID NO: 11).

D. Combinations of the Dual-Labeled THD Primer with an Internal Unlabeled Primer The real-time PCR reaction was the same used in the EXAMPLE 7A except the use of the internal primer (10 pmole, SEQ ID NO: 13).

As shown in FIGS. 15-18, the real-time signal amplification and target nucleic acid sequence amplification showed the applicability of various THD primer combinations on real-time PCR amplification.

Example 8

Comparison of Methods Using the THD Primer and the Taqman Probe in Real-Time PCR Amplification To investigate the mechanism of signaling, we compared the real-time PCR method of the present invention method using the THD primer with the TaqMan real-time PCR method by using *N. gonorrhoeae* gene as a target nucleic acid template.

The THD primer has a DPO structure with a dual label. The sequences of the dual-labeled THD primer, the TaqMan probe and the primer used in this EXAMPLE are:

NG-P1

(SEQ ID NO: 11)
5'-CAATGGATCGGTATCACTCGCIIIIICGAGCAAGAAC-3'

NG-THD1

(SEQ ID NO: 12)
5'-[6-FAM]CAATGGATCGG[BHQ1-dT]ATCACTCGCIIIIICGAGCAGAAC-3'

NG-P2

(SEQ ID NO: 13)
5'-ATTGGCGTGTTTCGCATATTTAAG-3'

NG-Probe (SEQ ID NO: 15)
5'-[6-FAM]ATTGGCGTGTTTCGCATA[BHQ1-dT]TTAAG[Phos-Q]-3'

NG-P3

(SEQ ID NO: 16)
5'-TACGCCTGCTACTTTCACGCTIIIIIGTAATCAGATG-3'

NG-THD3

(SEQ ID NO: 17)
5'-[6-FAM]TACGCCTGCTAC[BHQ1-dT]TTCACGCTIIIIIGTAATCAGATG-3'

Real-time PCR was conducted in the final volume of 20 μl containing 1 ng of genomic DNA of *N. gonorrhoeae*, 10 μl of 2× QIAGEN Multiplex Master Mix containing 6 mM MgCl$_2$, Taq DNA polymerase and dNTPs (QIAGEN), 10 pmole of primer (SEQ ID NO: 11) or dual-labeled THD primer (SEQ ID NO: 12) as a forward primer, 10 pmole of primer (SEQ ID NO: 16) or dual-labeled THD primer (SEQ ID NO: 17) as a reverse primer, 5 pmole of TaqMan probe (SEQ ID NO: 15) or internal primer (SEQ ID NO: 13) as a internal probe/primer; the tube containing the reaction mixture was placed in the real-time thermocycler (CFX96, Bio-Rad); the reaction mixture was denatured for 10 min at 95° C. and subjected to 20 cycles of 30 sec at 94° C., 90 sec at 60° C. and 90 sec at 72° C. Detection of the generated signal was performed at the extension step (72° C.) of each cycle.

As shown in FIG. 19, the various THD primer combinations were proven to amplify target nucleic acid sequence. Moreover, the signal amplification occurs with a great efficiency (No. 2, 3, 5 and 6) in the absence of dual-label probe which is usually required for TaqMan probe method (No. 4). I.e. it not only showed the lower Ct value compared to TaqMan probe reaction, but also higher intensity of florescent signal. Therefore, unlike the existing TaqMan probe method, it is possible to amplify target signal and target nucleic acid sequence with a greater efficiency, only by using the primer which is designed to amply the target nucleic acid sequence.

Having described a preferred embodiment of the present invention, it is to be understood that variants and modifications thereof falling within the spirit of the invention may become apparent to those skilled in this art, and the scope of this invention is to be determined by appended claims and their equivalents.

---

What is claimed is:

1. A method for detecting a target nucleic acid sequence from a DNA or a mixture of nucleic acids using a 5'-cleavage reaction and a 3'-extension reaction of a target hybridization and detection primer (THD primer), which comprises the steps of:
   (a) hybridizing the target nucleic acid sequence with the THD primer in the absence of an additional primer located upstream from the THD primer; wherein the THD primer comprises (i) a hybridizing nucleotide sequence complementary to the target nucleic acid sequence and (ii) a label or an interactive label system containing a plurality of labels;
   (b) contacting the resultant of step (a) to a template-dependent nucleic acid polymerase having a 5' to 3' nuclease activity under conditions for the 5'-cleavage reaction and the 3'-extension reaction of the THD primer by the template-dependent nucleic acid polymerase; wherein the THD primer is extended by the polymerase activity of the template-dependent nucleic acid polymerase and cleaved by the 5' to 3' nuclease activity of the template-dependent nucleic acid polymerase to release the label, or at least one label of the interactive label system from the THD primer, whereby a signal indicative of the presence of the target nucleic acid sequence is obtained; and
   (c) detecting the signal indicative of the presence of the target nucleic acid sequence.

2. The method according to claim 1, wherein the method further comprises repeating the steps (a)-(b) or (a)-(c) with denaturation between repeating cycles at least twice to amplify the signal indicative of the presence of the target nucleic acid sequence.

3. The method according to claim 1, wherein the THD primer has a dual priming oligonucleotide (DPO) structure represented by the following general formula I or a modified dual specificity oligonucleotide (mDSO) structure represented by the following general formula II:

5'-Xp-Yq-Zr-3'     (I)

wherein, Xp represents a 5'-first priming portion having a hybridizing nucleotide sequence complementary to the target nucleic acid; Yq represents a separation portion comprising at least three universal bases, Zr represents a 3'-second priming portion having a hybridizing nucleotide sequence complementary to the target nucleic acid; p, q and r represent the number of nucleotides, and X, Y, and Z are deoxyribonucleotides or ribonucleotides; the Tm of the 5'-first priming portion is higher than that of the 3'-second priming portion and the separation portion has the lowest Tm in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the THD primer is enhanced;

5'-X'p-Y'q-Z'r-3'     (II)

wherein, X'p represents a 5'-second priming portion having a hybridizing nucleotide sequence complementary to the target nucleic acid sequence; Y'q represents a separation portion comprising at least three universal bases, Z'r represents a 3'-first priming portion having a hybridizing nucleotide sequence complementary to the target nucleic acid sequence; p, q and r represent the number of nucleotides; and X', Y' and Z' are deoxyribonucleotides or ribonucleotides; the Tm of the 5'-second priming portion is lower than that of the 3'-first priming portion and the separation portion has the lowest Tm in the three portions of X'p, Y'q and Z'r; the separation portion separates the 5'-second priming portion from the 3'-first priming portion in terms of annealing events to the target nucleic acid sequence, the annealing specificity of the oligonucleotide are determined dually by the 5'-second priming portion and the 3'-first priming portion such that the overall annealing specificity of the THD primer is enhanced.

4. The method according to claim 1, wherein the THD primer comprises at least one label on its 5'-end portion.

5. The method according to claim 4, wherein the THD primer comprises at least one label at its 5'-end.

6. The method according to claim 1, wherein the interactive label system is a pair of a fluorescent reporter molecule and a quencher molecule positioned on the THD primer to quench the fluorescence of the reporter molecule, and the two labels are separated by a site within the THD primer susceptible to nuclease cleavage, wherein the 5' to 3' nuclease activity of the template-dependent nucleic acid polymerase separates the fluorescent reporter molecule from the quencher molecule by cleaving at the susceptible site, thus generating the signal indicative of the presence of the target nucleic acid sequence.

7. The method according to claim 6, wherein the fluorescent reporter molecule is located on a 5'-end portion of the THD primer and the quencher molecule is located downstream from the fluorescent reporter molecule.

8. The method according to claim 6, wherein the quencher molecule is located on a 5'-end portion of the THD primer and the fluorescent reporter molecule is located downstream from the quencher molecule.

9. The method according to claim 1, wherein the target nucleic acid sequence comprises at least two types of nucleic acid sequences and the THD primer comprises at least two types of primers.

10. The method according to claim 1, wherein the target nucleic acid sequence comprises a nucleotide variation.

11. The method according to claim 1, wherein the target nucleic acid sequence is a pre-amplified nucleic acid sequence.

12. A method for detecting a target nucleic acid sequence from a DNA or a mixture of nucleic acids using a 5'-cleavage reaction and a 3'-extension reaction of a target hybridization and detection primer (THD primer), which comprises the steps of:
(a) hybridizing the target nucleic acid sequence with a primer pair composed of two primers as a forward primer and a reverse primer in which at least one primer is the THD primer capable of amplifying the target nucleic acid sequence; wherein the THD primer comprises (i) a hybridizing nucleotide sequence complementary to the target nucleic acid sequence and (ii) a label or an interactive label system containing a plurality of labels; wherein the hybridization is carried out in the absence of an additional primer located upstream from the THD primer;
(b) contacting the resultant of step (a) to a template-dependent nucleic acid polymerase having a 5' to 3' nuclease activity under conditions for the 5'-cleavage reaction and the 3'-extension reaction of the two primers by the template-dependent nucleic acid polymerase, wherein the two primers are extended by the polymerase activity of the template-dependent nucleic acid polymerase and cleaved by the 5' to 3' nuclease activity of the template-dependent nucleic acid polymerase to release the label, or at least one label of the interactive label system from the THD primer among the two primers, whereby a signal indicative of the presence of the target nucleic acid sequence is obtained;
(c) denaturing the resultant of step (b);
(d) repeating the steps (a)-(c) at least twice to amplify both the target nucleic acid sequence and the signal indicative of the presence of the target nucleic acid sequence; and
(e) detecting the signal indicative of the presence of the target nucleic acid sequence, wherein the detection is performed for each cycle of the repetition of step (d), at the end of the repetition of step (d) or at each of predetermined time intervals during the repetition, such that the signal is indicative of the presence of the target nucleic acid sequence.

13. The method according to claim 12, wherein the THD primer has a dual priming oligonucleotide (DPO) structure represented by the following general formula I or a modified dual specificity oligonucleotide (mDSO) structure represented by the following general formula II:

$$5'\text{-}Xp\text{-}Yq\text{-}Zr\text{-}3' \qquad (I)$$

wherein, Xp represents a 5'-first priming portion having a hybridizing nucleotide sequence complementary to the target nucleic acid; Yq represents a separation portion comprising at least three universal bases, Zr represents a 3'-second priming portion having a hybridizing nucleotide sequence complementary to the target nucleic acid; p, q and r represent the number of nucleotides, and X, Y, and Z are deoxyribonucleotides or ribonucleotides; the Tm of the 5'-first priming portion is higher than that of the 3'-second priming portion and the separation portion has the lowest Tm in the three portions; the separation portion separates the 5'-first priming portion from the 3'-second priming portion in terms of annealing events to the target nucleic acid, whereby the annealing specificity of the oligonucleotide are determined dually by the 5'-first priming portion and the 3'-second priming portion such that the overall annealing specificity of the THD primer is enhanced;

$$5'\text{-}X'p\text{-}Y'q\text{-}Z'r\text{-}3' \qquad (II)$$

wherein, X'p represents a 5'-second priming portion having a hybridizing nucleotide sequence complementary to the target nucleic acid sequence; Y'q represents a separation portion comprising at least three universal bases, Z'r represents a 3'-first priming portion having a hybridizing nucleotide sequence complementary to the target nucleic acid sequence; p, q and r represent the number of nucleotides; and X', Y' and Z' are deoxyribonucleotides or ribonucleotides; the Tm of the 5'-second priming portion is lower than that of the 3'-first priming portion and the separation portion has the lowest Tm in the three portions of X'p, Y'q and Z'r; the separation portion separates the 5'-second priming portion from the 3'-first priming portion in terms of annealing events to the target nucleic acid sequence, the annealing specificity of the oligonucleotide are determined dually by the 5'-second priming portion and the 3'-first priming portion such that the overall annealing specificity of the THD primer is enhanced.

14. The method according to claim 12, wherein the THD primer comprises at least one label on its 5'-end portion.

15. The method according to claim 14, wherein the THD primer comprises at least one label at its 5'-end.

16. The method according to claim 12, wherein the interactive label system is a pair of a fluorescent reporter molecule and a quencher molecule positioned on the THD primer to quench the fluorescence of the reporter molecule, and the two labels are separated by a site within the THD primer susceptible to nuclease cleavage, wherein the 5' to 3' nuclease activity of the template-dependent nucleic acid polymerase separates the fluorescent reporter molecule from the quencher molecule by cleaving at the susceptible site, thus generating the signal indicative of the presence of the target nucleic acid sequence.

17. The method according to claim 16, wherein the fluorescent reporter molecule is located on a 5'-end portion of the THD primer and the quencher molecule is located downstream from the fluorescent reporter molecule.

18. The method according to claim 16, wherein the quencher molecule is located on a 5'-end portion of the THD primer and the fluorescent reporter molecule is located downstream from the quencher molecule.

19. The method according to claim 12, wherein the target nucleic acid sequence comprises at least two types of nucleic acid sequences and each of the two primers as the forward primer and the reverse primer comprises at least two types of primers.

20. The method according to claim 12, wherein the target nucleic acid sequence comprises a nucleotide variation.

21. A method for detecting a target nucleic acid sequence from a DNA or a mixture of nucleic acids using a polymerase chain reaction (PCR) associated with a 5'-cleavage reaction and a 3'-extension reaction of a target hybridization and detection primer (THD primer), which comprises the steps of:
(a) preparing a PCR mixture containing the target nucleic acid sequence, a primer pair composed of two primers as a forward primer and a reverse primer in which at least one primer is the THD primer capable of amplifying the target nucleic acid sequence, and a template-dependent nucleic acid polymerase having a 5' to 3' nuclease activity; wherein the THD primer comprises (i) a hybridizing nucleotide sequence complementary to the target nucleic acid sequence and (ii) a pair of a fluorescent reporter molecule and a quencher molecule positioned on the THD primer to quench the fluorescence of the reporter molecule; wherein the two labels are separated by a site within the THD primer susceptible to nuclease cleavage, wherein the 5' to 3' nuclease activity of the template-dependent nucleic acid polymerase separates the fluorescent reporter molecule from the quencher molecule by cleaving at the susceptible site, thus generating the signal indicative of the presence of the target nucleic acid sequence;
(b) amplifying the target nucleic acid sequence using the PCR mixture by performing at least two cycles of primer annealing, primer extending and denaturing, wherein the two primers are extended by the polymerase activity of the template-dependent nucleic acid polymerase to amplify the target nucleic acid sequence and cleaved by the 5' to 3' nuclease activity of the template-dependent nucleic acid polymerase to release the reporter molecule or the quencher molecule from the THD primer among the two primers, whereby a signal indicative of the presence of the target nucleic acid sequence is obtained; wherein the amplification is carried out in the absence of an additional primer located upstream from the THD primer; and
(c) detecting the fluorescence signal indicative of the presence of the target nucleic acid sequence, wherein the detection is performed for each cycle of the repetition of step (b), at the end of the repetition of step (c) or at each of predetermined time intervals during the repetition, such that the signal is indicative of the presence of the target nucleic acid sequence.

* * * * *